United States Patent
Liu et al.

(10) Patent No.: US 11,564,392 B2
(45) Date of Patent: Jan. 31, 2023

(54) METHODS OF INACTIVATION OF VIRUSES USING N-METHLYGLUCAMIDE AND ITS DERIVATIVES

(71) Applicant: BAYER HEALTHCARE LLC, Indianola, PA (US)

(72) Inventors: Shengjiang Liu, Lafayette, CA (US); Allison Titong, Hayward, CA (US); Wensheng Wang, Pittsburg, CA (US); Nicholas Spadoni, Pleasant Hill, CA (US)

(73) Assignee: Bayer Healthcare LLC, Whippany, NJ (US)

( * ) Notice: Subject to any disclaimer, the term of this patent is extended or adjusted under 35 U.S.C. 154(b) by 113 days.

(21) Appl. No.: 16/646,600

(22) PCT Filed: Sep. 12, 2018

(86) PCT No.: PCT/US2018/050579
§ 371 (c)(1),
(2) Date: Mar. 12, 2020

(87) PCT Pub. No.: WO2019/055463
PCT Pub. Date: Mar. 21, 2019

(65) Prior Publication Data
US 2020/0260727 A1    Aug. 20, 2020

Related U.S. Application Data

(60) Provisional application No. 62/559,812, filed on Sep. 18, 2017.

(51) Int. Cl.
*A01N 37/20* (2006.01)
*C12N 7/00* (2006.01)

(52) U.S. Cl.
CPC .............. *A01N 37/20* (2013.01); *C12N 7/00* (2013.01)

(58) Field of Classification Search
None
See application file for complete search history.

(56) References Cited

U.S. PATENT DOCUMENTS

| | | | |
|---|---|---|---|
| 5,254,339 | A | 10/1993 | Morein |
| 5,648,472 | A | 7/1997 | Gehringer et al. |
| 5,650,270 | A | 7/1997 | Giese et al. |
| 5,733,885 | A | 3/1998 | Eibl et al. |
| 2002/0127587 | A1 | 9/2002 | Simms et al. |
| 2008/0044807 | A1 | 2/2008 | Aoyagi et al. |
| 2008/0193916 | A1 | 8/2008 | Maki et al. |
| 2009/0017443 | A1 | 1/2009 | Ohue et al. |
| 2015/0306223 | A1 | 10/2015 | Conley et al. |
| 2016/0333046 | A1 | 11/2016 | Fisher et al. |

FOREIGN PATENT DOCUMENTS

| | | |
|---|---|---|
| CN | 101332297 B | 8/2011 |
| JP | 2005164496 A | 6/2005 |
| JP | 2010077091 A | 4/2010 |
| JP | 2016182112 A | 10/2016 |
| KR | 920006107 A | 4/1992 |
| WO | 9516205 A1 | 6/1995 |
| WO | 9704815 A1 | 2/1997 |
| WO | 9741891 A1 | 11/1997 |
| WO | 9966918 A1 | 12/1999 |
| WO | 0024377 A1 | 5/2000 |
| WO | 2008076371 A2 | 6/2008 |
| WO | 2009131995 A1 | 10/2009 |
| WO | 2010014903 A1 | 2/2010 |
| WO | 2013006797 A1 | 1/2013 |
| WO | 2015036549 A1 | 3/2015 |
| WO | 2015073633 A1 | 5/2015 |

OTHER PUBLICATIONS

"Search Report and Written Opinion for Corresponding Singapore Application 11202002449P dated Sep. 2, 2021".
Emd; Millipore., "Solvent-Detergent Viral Inactivation of Plasma-Derived Products in Mobius® Single-Use Process Containers", 2015, 1-8.
Korneyeva; et al., "Enveloped Virus Inactivation by Caprylate: A Robust Alternative to Solvent-Detergent Treatment in Plasma Derived Intermediates", Biologicals, vol. 30, 153-162.
Anderson; et al, "Presence and Transcription of Intracistemal A-Particle-Related Sequences in CHO Cells", Journal of Virology, May 1990, vol. 64 No. 5, 2021-2032.
Arnold; P., "The Use and Effects of Ecofriendly Surfactants in the Meat Rendering Industry in the United States.", Electronic Theses and Dissertations, May 2012, Paper 47.
Banerjee; et al, "Differential Solubilization of Lipids Along with Membrane Proteins by Different Classes of Detergents", Chemistry and Physics of Lipids, 1995, vol. 77, 65-78.

(Continued)

*Primary Examiner* — Brian J Davis

(57) ABSTRACT

This disclosure relates to methods for use in inactivating viruses. The methods of inactivating viruses with N-methylglucamides is applicable to the purification process of biologically-active drugs such as protein subunits, proteins (enzymes, factors, etc.), recombinant proteins, antibodies, vaccine or gene therapeutic products. The detergents used in this method are based on multiple N-methylglucamide homologs, consisting of a hydrophilic glucose moiety and hydrophobic fatty acid tail, linked by an amide bond. Additionally, these sugar-based detergents are nonionic by nature, which do not disrupt the drug protein, plasma biologies, non-enveloped viral vaccine or adeno associated viral particles. A method of purifying a biological product solution of interest having an unidentified enveloped virus contaminant, including incubating a biological product solution of interest with a standard solution, inactivating any potential enveloped virus contaminant present in the biological product solution of step (a), measuring the inactivated virus present in the final solution of step (b), incubating a separate biological product solution of interest with a N-methylglucamide solution, measuring the inactivated virus present in the final solution of step (d), and comparing the results of the final solutions of step (c) and step (e).

13 Claims, 17 Drawing Sheets

(56) References Cited

OTHER PUBLICATIONS

Basu; et al, "On Mixed Binary Surfactant Systems Comprising MEGA 10 and Alkyltrimethylammonium Bromides: A Detailed Physicochemical Study with a Critical Analysis", Journal of Colloid and Interface Science, 2007, vol. 307, 543-553.

Boschetti; et al, "Virus Safety of Intravenous Immunoglobulin", Clinical Reviews in Allergy & Immunology, 2005, vol. 29, 333-344.

Chan; S. Y., "Characterization of Recombinant BHK-21 Endogenous Particles: R-type Particles", Biologicals, 1994, vol. 22, 121-125.

Chou; et al, "TnBP/Triton X-45 Treatment of Plasma for Transfusion Efficiently Inactivates Hepatitis C Virus", Plos One, Feb. 6, 2015, 1-15.

Chuang; et al, "Optimal Concentrations of N-Decanoyl-N-Methylglucamine and Sodium Dodecyl Sulfate Allow the Extraction and Analysis of Membrane Proteins", Analytical Biochemistry, Aug. 10, 2011, vol. 418, 298-300.

Conley; et al, "Evaluation of Eco-Friendly Zwitterionic Detergents for Enveloped Virus Inactivation", Biotechnology and Bioengineering, Apr. 2017, vol. 114 No. 4, 813-820.

Dichtelmuller; et al., "Effective Virus Inactivation and Removal by Steps of Biotest Pharmaceuticals IGIV Production Process", Results in Immunology, Jan. 16, 2012, vol. 2, 19-24.

Durno; et al., "Viral Inactivation: Low pH and Detergent", PDA Journal of Pharmaceutical Science and Technology, 2015, vol. 69 No. 1, 163-172.

Elthon; et al, "Characterization and Solubilization of the Alternative Oxidase of Sauromatum guttatum Mitochondria", Plant Physiology, 1986, vol. 82, 1-6.

Emd; Millipore., "Solvent-Detergent Viral Inactivation of Plasma-Derived Products in Mobius® Single-Use Process Containers", Application Note, 2015, 1-8.

Farhana; et al., "Development of Safer Surfactant Alternatives to Octyl Phenol Ethoxylates for Immunoassay Applications", 10th Greener Materials Research Symposium: Lowell, MA, May 10, 2017, 1-7.

Foster; et al., "Factor VIII Structure and Function", Blood Reviews, 1989, vol. 3, 180-191.

Gaber; et al, "Environmentally Evaluated HPLC-ELSD Method to Monitor Enzymatic Synthesis of a Non-ionic Surfactant", Chemistry Central Journal, 2014, vol. 8 No. 33, 1-8.

Gaber; et al, "Enzymatic Synthesis of N-alkanoyl-N-methylglucamide Surfactants: Solvent-Free Production and Environmental Assessment", Green Chemistry, 2010, vol. 12, 1817-1825.

Goldoni; et al, "Effect of Various Detergents on the Interaction Between BK Virus and Susceptible Cells", Microbiologica, 1994, vol. 17 No. 3, 187-193.

"Guidelines on Viral Inactivation and Removal Procedures Intended to Assure the Viral Safety of Human Blood Plasma Products", World Health Organization Technical Report, 2004, Series No. 924, 150-224.

Hill; et al., "Sugar-Based Surfactants for Consumer Products and Technical Applications", European Journal of Lipid Science and Technology, 1999, vol. 101, 25-33.

Hjelmeland; et al., "A New Class of Nonionic Detergents with a Gluconamide Polar Group", Analytical Biochemistry, 1983, vol. 130, 485-490.

Hsieh; et al, "Detection of Cache Valley Virus in Biologies Manufactured in CHO Cells", BioPharm International, Oct. 2008, vol. 21 No. 10, 89-94.

Jeffrey; et al, "The Structures of 1-deoxy-(N-methyloctanamido)-d-glucitol (MEGA-8) and 1-deoxy-(N-methylundecanamido)-d-glucitol (MEGA-11)", Acta Crystallographica Section B: Structural Science, Apr. 12, 1989, vol. 45, 447-452.

Korneyeva; et al, "Enveloped Virus Inactivation by Caprylate: A Robust Alternative to Solvent-Detergent Treatment in Plasma Derived Intermediates", Biologicals, 2002, vol. 30, 153-162.

Larson; P.J., "The Clinical Development of Recombinant Coagulation Factor VIII (Kogenate®) for the Treatment of Hemophilia A", Novel Therapeutic Proteins: Selected Case Studies, Dec. 2007, 203-224.

Li; et al, "PG-4 Cell Plaque Assay for Xenotropic Murine Leukemia Virus", Journal of Virological Methods, 1999, vol. 81, 47-53.

Liu; et al, "Development and Qualification of a Novel Virus Removal Filter for Cell Culture Applications", Biotechnology Progress, 2000, vol. 16, 425-434.

Liu; Shengjiang, "Explorations in Viral Filtration", Viral Clearance Symposium 2017, 2017, 1-10.

Liumbruno; et al, "Solvent/detergent plasma: pharmaceutical characteristics and clinical experience", Journal of Thrombosis and Thrombolysis, Feb. 19, 2015, vol. 39, 118-128.

Madsen; et al, "Biodegradability and Aquatic Toxicity of Glycoside Surfactants and a Nonionic Alcohol Ethoxylate", Journal of the American Oil Chemists Society, 1996, vol. 73 No. 7, 929-933.

Magae; et al, "3-O-alkyl-D-glucose Derivatives Induce Fruit Bodies of Pleurotus Ostreatus", Mycological Research, Mar. 2005, vol. 109 No. 3, 374-376.

Mahajan; et al, "Bridging Polymer Science to Biotechnology Applications: A Single-Use Technology Conference Report", BioProcess International, Oct. 15, 2018, vol. 16 No. 10, 12-21.

Mayner; et al, "Evaluation of the single radial-immunodiffusion assay for measuring the glycoprotein content of rabies vaccines", Journal of Biological Standardization, 1987, vol. 15 No. 1, 1-10.

McPherson; et al, "Searching for Silver Bullets: An Alternative Strategy for Crystallizing Macromolecules", Journal of Structural Biology, 2006, vol. 156 No. 3, 387-406.

Merza; et al, "Bovine Leukaemia Virus ISCOMs: Biochemical Characterization", Vaccine, Feb. 1989, vol. 7 No. 1, 22-28.

Miyagishi; et al, "Salt Effect on Critical Micelle Concentrations of Nonionic Surfactants, N-Acyl-N-methylglucamides (MEGA-n)", Journal of Colloid Interface Science, Feb. 27, 2001, vol. 238, 91-95.

Mohanty; et al, "Inhibition of Tobacco Etch Virus Protease Activity by Detergents", Protein Expression and Purification, 2003, vol. 27 No. 1, 109-114.

Molina-Bolivar; et al, "Self-Assembly, Hydration, and Structures in N-decanoyl-N-methylglucamide Aqueous Solutions: Effect of Salt Addition and Temperature", Journal of Colloid and Interface Science, 2007, vol. 313, 656-664.

Neurath; et al, "Characterization of Subviral Components Resulting from Treatment of Rabies Virus with Tri(n-butyl) Phosphate", Journal of General Virology, Jan. 1, 1972, vol. 14 No. 1, 33-48.

Nokta; et al, "Cytomegalovirus: Sodium Entry and Development of Cytomegaly in Human Fibroblasts", Virology, Feb. 2, 1988, vol. 164 No. 2, 411-419.

Qiu; et al, "Identification and Quantitation of Vesivirus 2117 Particles in Bioreactor Fluids from Infected Chinese Hamster Ovary Cell Cultures", Biotechnology and Bioengineering, 2013, vol. 110 No. 5, 1342-1353.

Ricco-Lattes; et al, "A Short Route to Analogs of Galactosphingolipids Possessing Anti-HIV and Anti-Aspergillus Activity", New Journal of Chemistry, 1995, vol. 19 No. 4, 341-344.

Roberts; P.L., "Virus Inactivation by Solvent/Detergent Treatment Using Triton X-100 in a High Purity Factor VIII", Biologicals, Jun. 13, 2008, vol. 36, 330-335.

Saito; et al, "Characteristics of n-octyl β-d-thioglucopyranoside, A New Non-Ionic Detergent Useful for Membrane Biochemistry", Biochemical Journal, Jul. 30, 1984, vol. 222, 829-832.

Scott; et al, "Inactivation of Enveloped Viruses—Seeking Alternatives to a Problematic Surfactant", BioProcess Intationational, Nov. 2018, 1-12.

Scott; C., "Sustainability in Bioprocessing: Not Just an Afterthought", BioProcess International, Nov. 1, 2011, vol. 9 No. 10, 24-36.

Soderlind; et al, "The Usefulness of Sugar Surfactants as Solubilizing Agents in Parenteral Formulations", International Journal of Pharmaceutics, 2003, vol. 252, 61-71.

Sofer; G., "Inactivation of Viruses: An Introduction to the Series", BioPharm International Supplement, Jun. 2003, vol. 16, S6-S7.

(56) References Cited

OTHER PUBLICATIONS

Sugihara; et al., "The CMC of the Mixed Systems of MEGA-9 with MEGA-10 in Water-10 in Water at 30° C.", Journal of Colloid and Interface Science, Jun. 1988, vol. 123, 544-545.
Suzuki; et al, "Molecular Cloning of Retrovirus-Like Genes Present in Multiple Copies in Syrian Hamster Genome", Nucleic Acids Research, 1982, vol. 10 No. 19, 5733-5746.
Tabarabaie; et al, "In Vivo Trapping of Nitric Oxide in the Brain of Neonatal Rats Treated with the HIV-1 Envelope Protein gp 120: Protective Effects of a-Phenyl-tert-butylnitrone", Biochemical and Biophysical Research Communications, Mar. 4, 1996, vol. 221 No. 2, 386-390.
Walter; et al, "Solubility Properties of the Alkylmethylglucamide Surfactants", Biochimica et Biophysica Acta (BBA)—Biomembranes, Apr. 20, 1990, vol. 1029, 67-74.
Wang; et al, "Endogenous Virus of BHK-21 Cells Complicates Electron Microscope Studies of Foamy Virus Maturation", Journal of Virology, Oct. 1999, vol. 73 No. 10, 8917.
Welling; et al, "Size-Exclusion High-Performance Liquid Chromatography of Sendai Virus Membrane Proteins in Different Detergents: A Comparison of Different Columns", Journal of Chromatography, 1986, vol. 359, 307-314.

METHODS OF INACTIVATION OF VIRUSES USING N-METHLYGLUCAMIDE AND ITS DERIVATIVES

BACKGROUND

Biotherapeutics are molecules produced from a process that involves raw materials of any kind of biological origin, i.e. cell lines, cell culture fluids, and tissue or body fluids. The manufacturing of biologically-derived therapeutics is a complex process that requires many purification steps to assure safety. It is especially important to consider there might be microbial contamination each step or process along the way. In case of recombinant protein production, the biotherapeutics are mostly made by the cultivation of engineered human or animal derived cells [i.e. Chinese hamster ovarian (CHO) or baby hamster kidney (BHK) cells] harboring a plasmid DNA containing the gene of interest (GOI), or hybridoma cells i.e. NS0, and a series of unit operations implementing the purification process. It is well known that CHO and BHK (Chan, S. Y., 1994, Wang G. et al 1999 & Suzuki A. et al 1982) cells have chromosomally integrated proviral elements coding endogenous retrovirus-like particles (ERVLPs). Biotherapeutics preparation from whole blood or plasma faces challenges of raw material contamination by blood borne pathogens i.e. hepatitis virus B (HBV), hepatitis C (HCV) viruses etc. In addition, adventitious agents might be introduced into manufacturing intermediates which create further challenges on the manufacturing. Thus far there are many reports of bioreactor viral contamination incidents (Hsieh, W. T. et al 2008, Qiu Y. et al, 2013). In particular, the inactivation and/or removal of viruses have plagued the biologics industry for many years. Some of the reasons include the variability in sources that the viruses are derived from as well as the small sizes.

Viruses are divided into enveloped and non-enveloped groups. Endogenous retrovirus-like particles are enveloped and found in the CHO and BHK cells and their related culture fluids which create a risk of contamination for further purification steps, facilities, instruments, and the environment. Though no infectivity has been observed using current methods, endogenous retrovirus-like particles present a potential risk to patients and to the industry. For all of these reasons it has become increasingly important to quickly and effectively inactivate and/or remove these contaminants from the manufacturing processes.

Detergents have been used as an important tool in inactivating viruses in a variety of arrays and assays. Beginning in the 1980s, detergents have increased the safety of blood sample pools (for patients in need of blood transfusions or blood components, such as plasma derived therapeutic products) and laboratory personnel handling the samples. More recently, detergents have been widely used in the manufacturing processes of biological therapeutics and/or vaccines that have the potential risk of viral contamination. In biological drug manufacturing, the most well-characterized and highly effective detergents used for the inactivation of enveloped viruses are nonionic detergents such as polysorbates (Tween-20, Tween-80), Triton X-100 (also known as Octoxinol-10) and tri-n-butyl phosphate (TnBP, often used as a solvent with polysorbates or Triton X-100). Polysorbates are highly effective in ambient conditions, but at a relatively high concentrations and potency decreases with lower temperatures. Therefore, these detergents may not be the best option for the manufacturing of biological materials that require lower temperature conditions which are important for stabilizing the biological activities and molecular structures.

Triton X-100 (also Octoxinol, Octoxinol-3, Preceptin) is a classic, well-established effective detergent in inactivating viruses. Triton X-100 together with its derivatives is highly potent at very low temperature. The octylphenol component of Triton-X 100 has been characterized to interact with the estrogen receptor leading to reproductive impacts in exposed animals. Bioprocess wastes containing Triton X-100 would cause negative consequences, especially for aquatic life if directly discharged into the environment. The treatment or recovery of the Triton X-100 from the bioprocess wastes would be very costly and troublesome. The pursuit of new environment friendly detergents (or non-ecotoxic) that effectively inactivate viruses without altering the bioactive drug has been a priority for many biopharmaceutical industries. Therefore, discovering effective, robust and environmentally safer detergents have been a high priority for biopharmaceutical industries.

SUMMARY

The embodiments of the present method comprise purifying a biological product solution of interest having an unidentified enveloped virus contaminant, comprising incubating the biological product solution of interest with an N-methylglucamide solution, inactivating any potential enveloped virus contaminant present in the biological product solution, and purifying the biological product solution.

A method of purifying a biological product solution of interest having an unidentified enveloped virus contaminant, comprising incubating a biological product solution of interest with a standard solution, inactivating any potential enveloped virus contaminant present in the biological product solution of step (a), measuring the inactivated virus present in the final solution of step (b), incubating a separate biological product solution of interest with a N-methylglucamide solution, measuring the inactivated virus present in the final solution of step (d), and comparing the results of the final solutions of step (c) and step (e).

BRIEF DESCRIPTION OF THE DRAWINGS

The skilled artisan will understand that the drawings, described below, are for illustration purposes only. The drawings are not intended to limit the scope of the present teachings or claims in any way.

DETAILED DESCRIPTION

Figure 1:
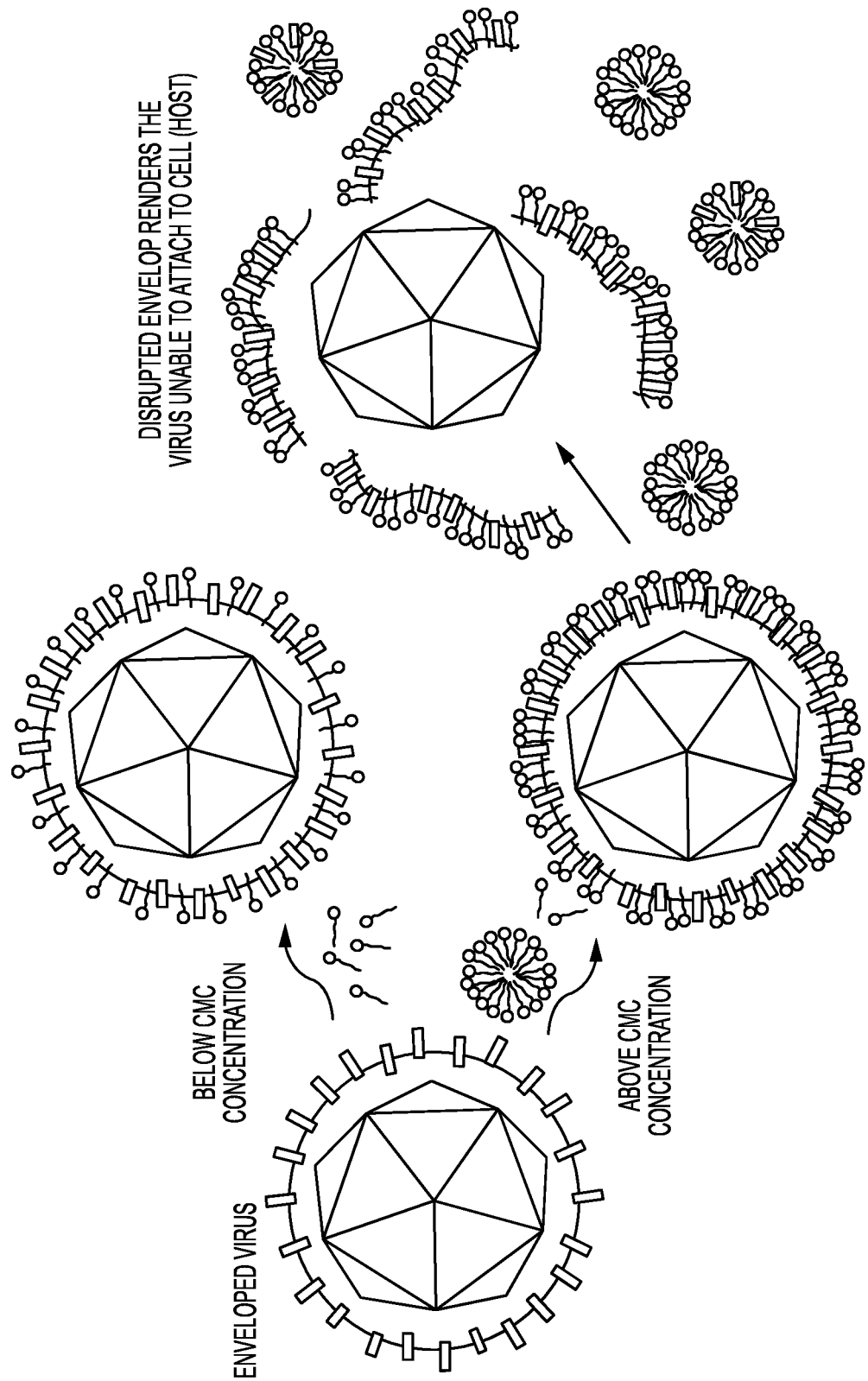
FIG. 1 shows a theoretical general mechanism for detergent disruption of enveloped viruses. Enveloped viruses such as retroviruses have an icosahedron-shaped nucleocapsid protected by a viral enveloped originating from the host cells and virus. Each detergent molecule has a hydrophilic head and hydrophobic tail, lending to its amphiphilic structure. The two portions determine the critical micelle concentration (CMC), which is a specific property of each detergent. Detergent monomers can insert within the virus envelope below a specified CMC and may or may not interfere with the attachment of the virus to the host. Conversely, at concentrations at or above CMCs, more detergent monomers can insert into the envelope and cause the disruption of the envelope, thereby rendering the virus unable to bind to its receptor on the host cell surface.

This disclosure provides methods and compositions which relate to viral inactivation.

Definitions

For the purpose of interpreting this specification, the following definitions will apply. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used).

Whenever appropriate, terms used in the singular will also include the plural and vice versa. The use of "a" herein means "one or more" unless stated otherwise or where the use of "one or more" is clearly inappropriate. The use of "or" means "and/or" unless stated otherwise. The use of "comprise," "comprises," "comprising," "include," "includes," and "including" are interchangeable and are not limiting. The terms "such as," "for example," and "e.g." also are not intended to be limiting. For example, the term "including" shall mean "including, but not limited to."

As used herein, the term "about" refers to +/−10% of the unit value provided.

As used herein, the term "substantially" refers to the qualitative condition of exhibiting a total or approximate degree of a characteristic or property of interest. One of ordinary skill in the biological arts will understand that biological and chemical phenomena rarely, if ever, achieve or avoid an absolute result because of the many variables that affect testing, production, and storage of biological and chemical compositions and materials, and because of the inherent error in the instruments and equipment used in the testing, production, and storage of biological and chemical compositions and materials. The term "substantially" is, therefore, used herein to capture the potential lack of completeness inherent in many biological and chemical phenomena.

Since the 1980s, detergents have been used as an essential tool to inactivate viruses in pooled blood collected from blood donors. This process is important for the safety of the patients receiving the blood, plasma or blood/plasma derived components, such as plasma derived Factor VIII (pdFVIII). Additionally, this purification measure increases the safety for the personnel directly involved in the processing of the blood in clinical laboratories or in manufacturing facilities of plasma derived biological products (PDBP). More recently, this practice has also become integral for the biopharmaceutical drug manufacturing process for biological therapeutics or vaccines comprising animal-derived materials. Animal-derived materials (i.e. blood, plasma, tissues, and proteins produced in mammalian cells) may carry endogenous viruses or may easily become contaminated with adventitious viruses. Therefore, the drug manufacturing process comprises a series of effective virus inactivation (i.e. solvent-detergent, low pH, and heat treatments) and removal technologies (i.e. viral filtration) to ensure patients receive virus free treatments. These processes are vital to the safe public release of the biologically-derived therapeutic or vaccine products. Novel methods to increase the efficiency, robustness, and most importantly, the overall safety of these products are in great need. To meet these demands, a new method of using ecofriendly N-methylglucamide based detergents is characterized in this disclosure.

Detergents are amphiphilic molecules that consist of a hydrophilic (polar) head group and a hydrophobic (nonpolar) tail group. This universal structure allows for the interaction of detergents with other molecules, most notably, proteins or enveloped viruses in an aqueous solution. In basic science and applied technologies, detergents can be used as a solubilizing agent or as a stabilizing agent to prevent biological molecule from aggregation or to solubilize membrane proteins from cell cultures or tissue suspensions. When used for solubilizing proteins, the following properties make certain detergents more desirable than others: 1) Detergents that lack charges (nonionic detergents) help retain the structure and activity of the protein of interest, 2) detergents with a low critical micelle concentration (CMC) allow for easy removal of the detergent via dialysis, 3) detergents that are clear and, therefore, do not affect protein absorbency readings, and 4) detergents that are highly pure, decreasing variability from experiment to experiment. Similarly, most of these properties are applicable when choosing detergent candidates for virus inactivation as it is necessary to not disrupt the protein drug, to detect protein concentration without interference from the detergent, and to ensure that the detergent is highly pure so viral inactivation consistently occurs.

Generally, enveloped virus inactivation is dependent on the amphiphilic structure and the critical micelle concentration (CMC) of the specific detergent. The CMC refers to the concentration at which detergent monomers aggregate to form micelle structures. In aqueous solutions, as more detergent monomers come in contact, the hydrophilic heads can adjoin to shield the hydrophobic tails from the aqueous solution, ultimately organizing into micelle structures. CMC is likely linked to the concentration at which viral inactivation will occur for a given detergent under specific conditions. A theoretical mechanism for virus inactivation is that the monomers insert into the viral envelope below the detergent CMC, which may be detrimental to the virus. As soon as the concentration is at or above the CMC, these detergent monomers present in the membrane form micelles that can disrupt the integrity or completely strip the viral envelope. Without the viral envelope, the virus is unable to bind to its receptor on the plasma membrane of its host cells and facilitate its replication and spread.

Thus far, the biotherapeutical manufacturing industry has used a number of detergents for inactivating enveloped viruses. One of the popular nonionic detergents Triton X-100 has been very effective at inactivating enveloped viruses without disrupting the protein drug. After the use of Triton X-100 in the biopharmaceutical manufacturing processes, it is disposed into the waste water treatment plants or is directly released into the aquatic environment (Madsen et al, 1996. JAOCS, 73:929-933). Unfortunately, the Triton X-100 by-product contains octylphenol which can mimic estrogen receptor substrates and can negatively impact the reproductive system of animals, especially aquatic life. Therefore, this detergent has been deemed a toxic chemical to the environment by a number of countries, which are starting to prohibit its use. Many biopharmaceutical industries have been dedicated to the search for environmentally safer detergents that have comparable efficacy to Triton X-100. For example, Biogen, Inc. and Genentech, Inc. have been looking into Lauryl dimethylamine N-oxide (LDAO) and alkyl glucosides, respectively (Conley et al., 2014, US Patent #WO2014025771A2; Conley et al., 2016, Biotechnol. Bioeng., Epub ahead of print; Fisher et al., 2016, US Patent #20160333046A1). While these companies have been able to distinguish new detergents of different classes, the present embodiments define a completely novel and highly effective class of nonionic detergents. N-methylglucamides (also known as fatty acid sugars), in the inactivation of enveloped viruses.

Sugar-based detergents have excellent physical properties, are highly biodegradable and non-toxic, which contribute to its safety profile, especially for the aquatic environment (Bogdan, 2007, Stalmans et al., 1993). Thus, the disclosed embodiments are focused on the use of the sugar-based detergents, N-methylglucamides, as a new method to inactivate viruses in bioactive-drug manufacturing.

N-methylglucamides are nonionic detergents that are composed of a highly hydrophilic glucose moiety and hydrophobic fatty acid chain linked by an amide bond. These detergents are ecofriendly as they are known to be highly biodegradable with about a 95% renewable carbon index and are considered non-toxic especially to aquatic life (Stalmans et al., 1993, SOFW, 119:794-808). Due to its increased safety profile and excellent physical properties, these detergents have gained heightened interest for use in basic science technologies, as well as for use in shampoos and dishwashing soaps. Likewise, these detergents could be prime candidates for viral inactivation of biologically-derived drug products.

The majority of recombinant proteins are produced by fermentation of genetically engineered mammalian cells (i.e. CHO and BHK). These cells are known to have chromosomally integrated retrovirus pro-viral genes or elements that produce endogenous retrovirus-like particles (ERVLPs) which are enveloped viral particles lacking confirmed infectivity. To demonstrate inactivation of ERVLPs, X-MuLV was used as a specific model for endogenous retroviruses and is currently used as a laboratory tool to assess the manufacturing purification process by spiking samples that are subjected to any inactivation or removal by given purification unit operation. As such, the disclosed embodiments will use this new method of using N-methylglucamides to inactivate the enveloped viruses, such as X-MuLV. Based on the X-MuLV model, all other enveloped viruses should all be susceptible to N-methylglucamide inactivation, including herpesviruses, flaviviruses, filoviruses, etc. Furthermore, this new method is applicable to any step throughout the drug purification process, which may involve a detergent removal step such as dialysis or column chromatography.

Generally, viral inactivation with this new class of detergent involves testing a laboratory strain of X-MuLV spiked into a protein sample (i.e. recombinant Factor VIII, human IgG antibody and plasma components) with N-methylglucamides, incubation of the sample at 2-8° C. for 30 minutes, and subsequent experimentation of the reaction tube on an indicator cell line (i.e. PG-4, Vero, or EBTr cell lines) to observe virus infection. The systematic approach for testing N-methylglucamides began with an initial screening under various conditions, followed by a protein activity assessment, dose response study, a kinetics study with high and low titer virus stocks, multiple viruses and biological application, and finally a multi-manufacturer comparison to ensure consistency. The initial screening conditions were based on the historical data for the classic Triton X-100 detergent, where virus inactivation was successful under 2-8° C., within 120 minutes, and an inactivation concentration that ranged from 0.1 to 0.3% (w/v). To ensure that the new detergents were comparable to a known potent detergent (Triton X-100), the low temperature and incubation for 30 and 120 minutes were chosen for the initial screen of the N-methylglucamides. The concentrations evaluated were based on the CMC of each new detergent. Then, the N-methylglucamide candidates that were most effective at inactivating enveloped virus were assessed for any effect on human Factor VIII activity, using a chromogenic assay kit. The N-methylglucamides were then assessed for their respective dose responses to increasing concentration of N-methylglucamides that ranged from 0.014-01.0% (w/v) with respect to each individual detergent. To assess how quickly inactivation occurs, kinetic studies were performed with the N-methylglucamides using both a low and high titer virus preparations. To increase the confidence of the data generated throughout the process, multiple vendor sources were assayed under similar conditions to demonstrate the consistency and reliability of the N-methylglucamides tested. Finally, to assess whether N-methylglucamides remained effective in other blood or plasma-related matrices, viral inactivation was determined in human immunoglobulin G and human plasma under similar conditions. Taken together, this systematic approach has enabled the disclosed embodiments to demonstrate the applicability of N-methylglucamides in the purification process.

This method of inactivating viruses with N-methylglucamides is applicable to the purification process of biologically-active drugs such as protein subunits, proteins (enzymes, factors, etc.), recombinant proteins, or antibodies. The environmentally safer (also called non ecotoxic) detergents used in this method are based on multiple N-methylglucamide homologs, consisting of a hydrophilic glucose moiety and hydrophobic fatty acid tail, linked by an amide bond. Since there are no known toxic intermediates such as octylphenol in N-methylglucamides, it eliminates the risks associated with environmental concerns when used in biologics production. Additionally, these sugar-based detergents are nonionic by nature, which should not disrupt of the drug protein of interest. This method involves the incubation of the N-methylglucamide with the biological product to inactivate any potential enveloped virus contaminant. To assess viral reduction by this method, model enveloped viruses (e.g. xenotropic leukemia virus, pseudorabies virus and bovine viral diarrheal virus) were spiked into a protein drug sample (e.g. native proteins, recombinant proteins, antibodies) and incubated with N-methylglucamides. After the incubation, a $TCID_{50}$ assay was performed to determine the viral titer and the log reduction factor (LRF) which is the difference of viral infectivity titers between non treated controls and N-mehtylglucamide treated samples. Furthermore, inactivation of enveloped viruses with N-methylclucamides is comparable to that of the industry standard, Triton X-100. Taken together, these excellent characteristics make N-methylglucamides a powerful tool in the purification process of biologically-derived drug products.

Materials

Example 1—Virus Stocks

Low and high titer xenotropic murine leukemia virus (X-MuLV) stocks, strain pNFS Th-1, were prepared internally in Bayer Pathogen Safety Laboratory (Berkeley, Calif.) or by Bioreliance Inc. (Rockville, Md.), respectively. High titer porcine pseudorabies virus (PPV) stock, strain Aujeszky, was prepared by Bioreliance Inc. (Rockville, Md.). High titer bovine viral diarrhea virus (BVDV) stock, strain NADL, was also prepared by Bioreliance Inc., (Rockville, Md.).

Example 2—Cell Lines

Feline PG-4 cells (S+L-) (ATCC CRL-2032), African Green Monkey Kidney Vero cells (ATCC CCL-81), and embryo bovine trachea EBTr cells (ATCC CCL-44) were purchased from American Type Culture Collection (ATCC, www.atcc.org).

Example 3—Cell Culture Medium and Supplements

The culture media used for PG-4, Vero and ETBr cells were McCoy's 5A (Lonza, 12-688F, Slough, UK) and Minutesimum Essential Medium Eagle (Corning, 10-010-CV, Manassas, Va.). The following growth medium supplements were used: Fetal Bovine Serum (FBS) (Hyclone, SH30070.03. Logan, Utah), 100× Penicillin/Streptomycin (P/S) (Corning, 30-002-Cl, Manassas, Va.), and 200 mM L-Glutaminutese (L-Glu) (MP Biomedicals, 1680149, Solon, Ohio).

Example 4—Chemicals

The chemical hexadimethrine bromide (Polybrene) (Sigma-Aldrich, H9268-5g, St. Louis, Mo.) was used to increase the efficiency of the X-MuLV infection in PG-4 cells and was added to McCoy's 5A medium at a final concentration of 3 µg/ml. The nonionic detergents characterized in this study are octanoyl-N-methylglucamide (Mega 8) (G-Biosciences, DG017, St. Louis, Mo. or Sigma or Sigma-Aldrich, St. Louis, Mo.), nonaoyl-N-methylglucamide (Mega 9) (G-Biosciences, DG019, St. Louis. Mo. or Sigma-Aldrich, St. Louis, Mo.), decanoyl-N-methylglucamide (Mega 10) (G-Biosciences, DG021, St. Louis, Mo. or Sigma-Aldrich. St. Louis, Mo.), dodecanoyl-N-methylglucamide (Mega 12) (Bachem, P-1175.0001, Torrance, Calif.), and P-tert-Octylphenoxy) polyethoxyethanol (Triton X-100) (EMD Millipore, 1086432500. Billerica, Mass.).

Biological Solutions:

Each virus inactivation assay was performed in the presence of a biological product solution consisting of either recombinant human factor VIII (rFVIII) (full length wild-type, Bayer in-house preparation), human IgG or plasma protein (Sigma-Aldrich. St. Louis, Mo.).

Methods

Example 1—Detergent Preparation

Mega 8, Mega 9, Mega 10 and Mega 12 detergents were prepared at a target concentration of 5% weight per volume (w/v) stock solution. Each detergent was obtained as powder from the manufacturer and was appropriately weighed and allowed to dissolve in Milli-Q water. If the detergent was not fully solubilized at room temperature, the solution was heated in a ≤37° C. water bath (Mega 10 and Mega 12) for about 10-15 minutes. Initially, 5% Mega 12 did not come into solution in at ≤37° C. and was, therefore, placed in a ≤60° C. water bath and the solution solubilized after 30 minutes. Since the critical micelle concentration of Mega 12 was at 0.013%, it was likely that at least a 10× stock solution would be convenient for use in virus inactivation. Therefore, a new stock solution prepared in Milli-Q water at a concentration of 0.15% which allowed the mixture to come into solution quicker when placed in a ≤60° C. water bath (about 15 minutes). The detergents were stored in a dark container in 2-8° C.

Example 2—Mega 8, Mega 9. Mega 10, and Mega 12 Virus Inactivation Screen

N-Methylglucamide detergents (Mega 8, Mega 9. Mega 10, and Mega 12) were evaluated for their ability to effectively and robustly inactivate xenotropic murine leukemia virus (X-MuLV), porcine pseudorabies virus (PRV), or bovine viral diarrhea disease virus (BVDV) under typical manufacturing conditions for recombinant Factor VIII (rFVIII) therapeutic drug. The concentrations tested for each detergent were based on 0.5×, 1×, or 2× of the critical micelle concentration (CMC), respectively. Each detergent was incubated with detergent-free rFVIII protein and spiked with a high-titer stock of X-MuLV at a ratio of 1:11 and incubated at 2.0±1.0° C. for 30 minutes. A positive control sample containing only rFVIII was included and incubated at 2.0±1.0° C. for 0 and 30 minutes. After each incubation time point, 40 µL of each inactivation sample or control was removed and transferred to a 15 mL tube containing 4.0 mL of basal medium (i.e. McCoy's 5A medium supplemented with 3 µg per mL polybrene (MP) for X-MuLV or EMEM). This 1:101 dilution factor quench allowed for the detergent to be diluted beyond the effects of toxicity to the indicator cell line and also allows for the virus to become diluted within the range necessary for performing $TCID_{50}$ assays. Briefly, the $TCID_{50}$ assay to assess virus infectivity was performed by titrating each quenched sample 1:3.2-fold serially in MP or EMEM up until the $11^{th}$ dilution level. A monolayer of indicator cells, seeded 1 day before at 3,000 cells per well in a 96 well cell culture plate, were inoculated with 100 µL per dilution of the quenched and serially diluted sample or basal medium, in replicates of 8. After 1.5-2.5 hour incubation at 37° C., 100 µL of assay medium consisting of basal medium (McCoy's 5A or EMEM for PRV or BVDV) supplemented with 4% FBS, 2% P/S, and 2% L-Glu was added to each well of the plate. Then the cells were incubated at 37° C. for up to 6-7 days and observed under light microscopy for the formation of cytopathic effects (CPE), which is indicative of virus infection.

Example 3—Chromogenic Assay to Assess Human Factor VIII Activity

Mega 10 was prepared at a concentration of 0.3% (w/v) in rFVIII matrix (from 5.0% (w/v) stock solutions prepared in Milli-Q $H_2O$) and incubated at 2.0±1.0° C. for 120 minutes. A diluent control of rFVIII matrix spiked only with Milli-Q $H_2O$ was also prepared and incubated under the same conditions. Following the incubation, detergents and diluent control were diluted in 1× assay buffer along with chromogenic assay (Chromogenix COATEST SP4 FVIII Kit, Cat: 82409463) FVIII standard and controls to the appropriate levels. Thirty µL of each detergent, control, and standard were loaded onto a 96-well plate in triplicate. Chromogenic assay reagents were added according to the manufacturer's protocol and incubated at 37.0° C. and 5.0% $CO_2$ for 8 minutes. Assay plate was measured for absorbance t 405 and 492 nm on a Molecular Devices SpectraMax M5 microplate reader. Data was analyzed using SoftMax Pro v5.

Example 4—Dose Response in rFVIII Triton Free Matrix

To assess the lowest effective concentration of the Mega10 detergent incubated with rFVIII and spiked with X-MuLV, a detergent dose response study was performed. A 0.5% (w/v) sample of each detergent was prepared in recombinant FVIII (rFVIII) matrix, followed by 1:2 serial dilutions in the rFVIII matrix to yield 6 samples of each detergent ranging from 0.014-0.5% (w/v). Additionally, a positive control sample containing the rFVIII matrix only was included. Each detergent sample and control was spiked with the low titer X-MuLV stock at a ratio of 1:11, and incubated at 2.0±1.0 C.° for 30 minutes. After the incubation, 100 µL of each inactivation sample and control was removed and transferred to 15 mL tubes containing 3.0 mL of McCoy's 5A medium supplemented with 3 µg per mL polybrene (MP). This 1:31 dilution factor quench allowed for the detergent to be diluted beyond the effects of toxicity to the indicator cell line (PG-4) and also allows for the X-MuLV to become diluted within the range necessary for performing $TCID_{50}$ assays. Briefly, the $TCID_{50}$ assay to assess X-MuLV infectivity was performed by titrating each quenched sample 1:3.2-hfold serially in MP up until the $11^{th}$ dilution level. A monolayer of PG-4 cells, seeded 1 day before at 3,000 cells per well, were inoculated with 100 µL per dilution of the quenched sample or MP, in replicates of 8. After incubation at 37° C. for 1.5-2.5 hr, 100 µL of assay medium consisting of McCoy's 5A medium supplemented with 4% FBS, 2% P/S, and 2% L-Glu was used to overlay the cells. Then the cells were incubated at 37° C. for up to 6-7 days and observed under light microscopy for the formation of cytopathic effects (CPE), which is indicative of X-MuLV infection.

Example 4—Virus Inactivation Kinetics

To assess inactivation rate of the Mega 10 detergent incubated with rFVIII and spiked with X-MuLV, virus inactivation kinetics studies were performed. A 0.02%, 0.10%, 0.20%, and 0.30% (w/v) sample of Mega 10 was prepared in recombinant FVIII (rFVIII) Triton free matrix.

Additionally, positive control samples containing the rFVIII matrix only or medium only control were included. Each detergent sample and control was spiked with the low titer and high titer X-MuLV stock at a ratio of 1:11, and incubated at 2.0±1.0 C° for 0, 5, 15, 30, 60, and 120 minutes. After each incubation, 100 or 40 µL of each inactivation sample and control was removed and transferred to 15 mL tubes containing 3.0 mL or 4.0 mL of McCoy's 5A medium supplemented with 3 µg per mL polybrene (MP). This 1:31 (low titer X-MuLV) or 1:101 (high titer X-MuLV) dilution factor quench allowed for the detergent to be diluted beyond the effects of toxicity to the indicator cell line (PG-4) and also allows for the X-MuLV to become diluted within the range necessary for performing a $TCID_{50}$ assay. Briefly, the $TCID_{50}$ assay to assess X-MuLV infectivity was performed by titrating each quenched sample 1:3.2 in MP up until the $11^{th}$ dilution level. A monolayer of PG-4 cells, seeded 1 day before at 3,000 cells per well, were inoculated with 100 µL per dilution of the quenched sample or MP, in replicates of 8. After 1.5-2.5 hr incubation at 37° C. and 5% $CO_2$, 100 µL of assay medium consisting of McCoy's 5A medium supplemented with 4% FBS, 2% P/S, and 2% L-Glu was used to overlay the cells. Then the cells were incubated at 37° C. and 5% $CO_2$ for up to 6-7 days and observed under light microscopy for the formation of cytopathic effects (CPE), which is indicative of X-MuLV infection.

Example-5—N-Methylglucamide Detergent Virus Inactivation in the Presence of Other Proteins N-methylglucamide detergents (Mega 8, Mega 9, Mega 10, and Mega 12) were evaluated for their ability to effectively and robustly inactivate X-MuLV, PRV or BVDV under typical manufacturing conditions for human plasma, plasma derived biologics or human antibodies. The concentrations tested for each detergent were based on 0.5×, 1×, or 2× of the critical micelle concentration (CMC), respectively. Each detergent was incubated with detergent- and multiple concentrations of free protein (high protein gradient) and spiked with a high-titer stock of X-MuLV at a ratio of 1:11 and incubated at 2.0±1.0° C. for 30 minutes. A positive control sample containing only the respective protein was included and incubated at 2.0±1.0° C. for 0 and 30 minutes. After each incubation time point, 40 µL of each inactivation sample or control was removed and transferred to a 15 mL tube containing 4.0 mL of basal medium (i.e. McCoy's 5A medium supplemented with 3 µg per mL polybrene (MP) for X-MuLV or EMEM for PRV or BVDV). This 1:101 dilution factor quench allowed for the detergent to be diluted beyond the effects of toxicity to the indicator cell line and also allows for the virus to become diluted within the range necessary for performing $TCID_{50}$ assays. Briefly, the $TCID_{50}$ assay to assess virus infectivity was performed by titrating each quenched sample 1:3.2-fold serially in basal medium (MP or EMEM) up until the 11th dilution level. A monolayer of indicator cells, seeded 1 day before at 3,000 cells per well, were inoculated with 100 µL per dilution of the quenched sample or basal medium, in replicates of 8. After 1.5-2.5 hr incubation at 37° C., 100 µL of assay medium consisting of basal medium (McCoy's 5A or EMEM) supplemented with 4% FBS, 2% P/S, and 2% L-Glu was used to overlay the cells. Then the cells were incubated at 37° C. for up to 6-7 days and observed under light microscopy for the formation of cytopathic effects (CPE), which is indicative of virus infection.

ASSAY EXAMPLES

Example 1: N-Methylglucamide Detergents: Properties, Preparation, and Evaluation Four methylglucamide-based detergents were analyzed for this study: octanoyl-N-methylglucamide (Mega 8), nonaoyl-N-methylglucamide (Mega 9), decanoyl-N-methylglucamide (Mega 10), and dodecanoyl-N-methylglucamide (Mega 12) (Table 1). These detergents are all the commercially available N-methylglucamides and multiple lots were purchased in powder-form from multiple vendors (G-Biosciences, Sigma, or Bachem).

FIG. 1 shows a proposed theoretical mechanism of how detergents can disrupt the envelopee of a virus. Generally, below the critical micelle concentration (CMC) of the respective detergent, the detergent monomers can insert within the viral envelope which may allow or abrogate the virus to attach to the cell (host). At concentrations above the CMC, more monomers insert into the virus envelope causing the complete disruption of the viral envelope, and monomers can form into micelles with themselves or with a mixture of micelles and viral proteins from the dismembered envelope. As described in the future examples within this patent, the CMC seems to be an indicator of the effective concentration (Example 3). At concentrations at or above the CMC, virus inactivation occurred with each of the methylglucamide detergents tested in this study.

Figure 2:
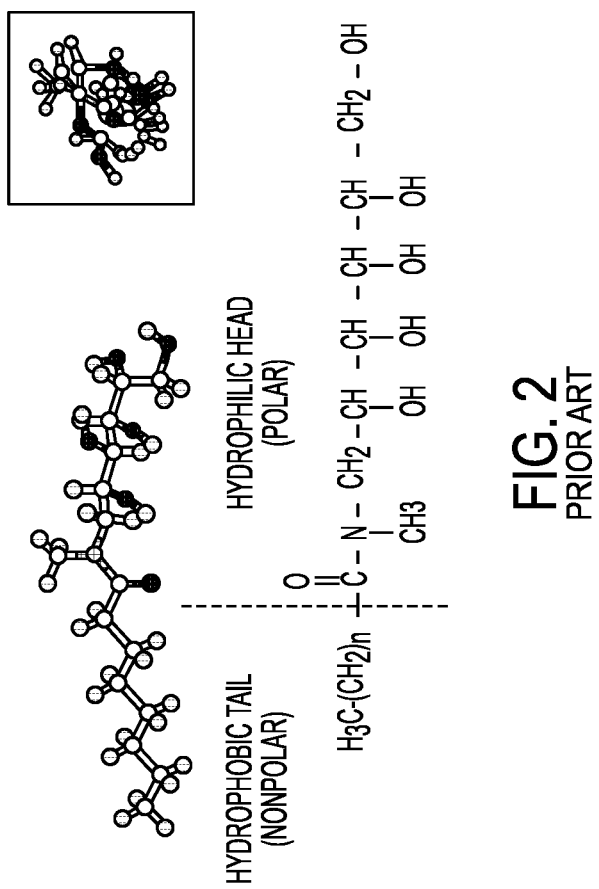
FIG. 2 shows the hydrophobic (nonpolar) and hydrophilic (polar) regions of an N-methylglucamide detergent.

N-methylglucamides contain an acyclic hydrophilic glucose polar head group and a hydrophobic fatty acid chain tail (consisting of 8-10, or 12 carbons), linked by an amide bond (FIG. 2). Based on Table 1, the N-methylglucamides are composed similarly, differing only in carbon chain length, which proportionally corresponds to the increase in molecular weight. Based on the work of others, as the carbons in the fatty acid chain increase, the critical micelle concentration (CMC) inversely decreases.

TABLE 1

Properties of Nonionic N-Methylglucamide Detergents

| Chemical Name | Trade Name | Molecular Formula | MW (Da) | CMC (mM, 25° C.) |
|---|---|---|---|---|
| Octanoyl-N-methylglucamide | Mega 8 | $C_{15}H_{31}NO_6$ | 321.4 | 58 |
| Nonaoyl-N-methylglucamide | Mega 9 | $C_{16}H_{33}NO_6$ | 335.4 | 19-25 |
| Decanoyl-N-methylglucamide | Mega 10 | $C_{17}H_{35}NO_6$ | 349.5 | 6-7 |
| Dodecanoyl-N-methylglucamide | Mega 12 | $C_{19}H_{39}NO_6$ | 377.5 | 0.35 |

Figure 3:
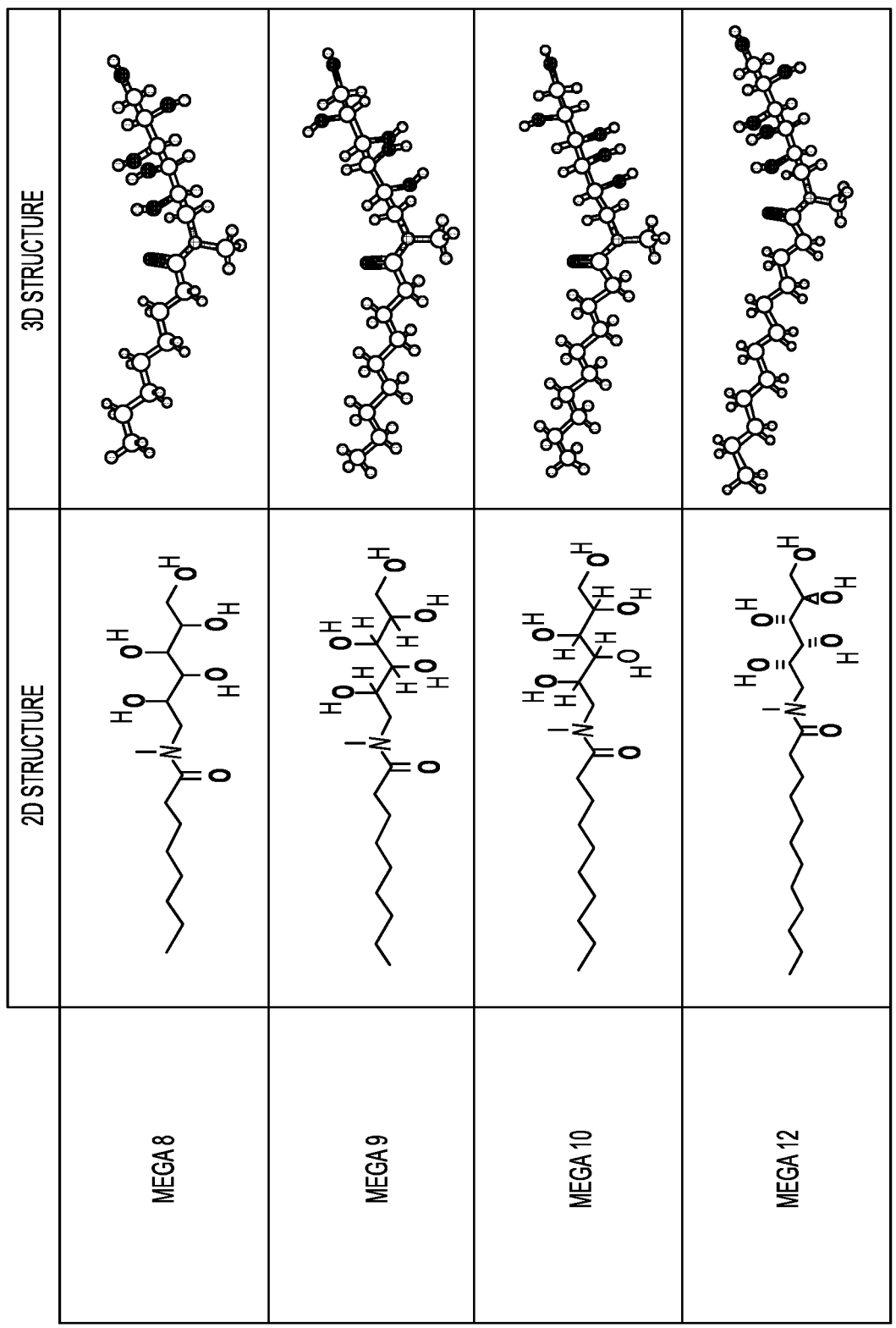
FIG. 3 shows the two-dimensional (2D) and three-dimensional (3D) structures of N-methylglucamide detergent homologs. Similarly, each compound is composed of a hydrophobic fatty acid chain consisting of 8-10 or 12 carbons that are linked by an amide bonded to an acyclic, hydrophilic glucose sugar moiety.

FIG. 3 shows the 2-dimensional (2D) and 3-dimensional (3D) structures of the N-methylglucamides used in this study. The 2D and 3D structures both show a similar arrangement of the carbon, hydrogen, oxygen and nitrogen molecules. Interestingly, the molecular packing of the between Mega 8 versus the others N-methylglucamides may form a head-to-head bilayer packing, whereas the others may pack with a head-to-tail monlayer packing. (Jeffery and Malusynksa, 1988. Acta Cryst., B45:447-452). This difference in packing may contribute to the increased potency as the carbon chain increase.

Table 2 lists the manufacturers of the detergent powders and the in-house preparation which are also detailed in the methods section. Of the 5% (weight by volume, w/v) detergents prepared, Mega 8 and Mega 9 were readily solubilized in water at room temperature. It was necessary for Mega10 to be warmed in a 37° C. water bath that allowed the solution to solubilize within 15 minutes. However, the Mega 12 was not able to dissolve water in a 37° C. water bath and was gradually solubilized in a 60° C. water bath for at least 5 minutes. This occurrence has been observed by others as well and may have to do with the increasing fatty chain length that enhances the hydrophobicity thus decreasing the likelihood of solubility, especially in water (Gaber et al., Burczyk, 2007). Therefore, a new 0.15% stock was prepared in Milli-Q water, which is at least 10× of the CMC. This new preparation was able to come into solution when placed in a 60° C. water bath within 15 minutes.

TABLE 2

Preparation and Storage of Detergents

| Detergent | Vendor, Cat # | Target Conc. | Mass (gm) | Vol. of Milli-Q water | Storage Condition |
|---|---|---|---|---|---|
| Mega 8 | G-Bioscience, DG017 | 5% | 0.5 | 9.5 | 2-8° C. |
| Mega 8 | Sigma, O3129-5G | 5% | 0.2 | 4.0 | 2-8° C. |
| Mega 8 | Sigma, O3129-5G | 5% | 0.5 | 10.0 | 2-8° C. |
| Mega 8 | Sigma, O3129-5G | 20% | 0.8 | 4.0 | 2-8° C. |
| Mega 9 | G-Bioscience, DG019 | 5% | 0.7 | 13.9 | 2-8° C. |
| Mega 9 | Sigma, N1138-5G | 5% | 0.3 | 4.0 | 2-8° C. |
| Mega 9 | Sigma, N1138-5G | 5% | 0.5 | 10.0 | 2-8° C. |
| Mega 10 | G-Bioscience, DG021 | 5% | 0.8 | 14.4 | 2-8° C. |
| Mega 10 | Sigma, D6277-5G | 5% | 0.2 | 4.0 | 2-8° C. |
| Mega 10 | Sigma, D6277-5G | 5% | 0.5 | 10.0 | 2-8° C. |
| Mega 12 | Bachem, 4065417.0001 | 5% | 1.0 | 18.2 | 2-8° C. |
| Mega 12 | Bachem, 4065417.0001 | 0.15% | 0.15 | 100.0 | 2-8° C. |
| Mega 12 | Bachem, 4065417.0001 | 0.15% | 0.15 | 100.0 | 2-8° C. |

Example 2: Viruses: Background and Properties

There are many enveloped RNA and DNA viruses that exist, such as those belonging within the following viral families: Retroviridae, Flaviviridae, Togaviridae, Coronaviridac, Filoviridac, Rhabdoviridac, Bunyaviriae, Orthomyxoviridae, Paramyxoviridea, Arenaviridae, Hepadnaviridae, Herpesviridae, Baculoviridae and Poxviridae. Many blood-borne viruses from any of these families could potentially contaminate animal-derived products used in the manufacturing of biologically active drug products. Therefore, many pharmaceutical companies have used model viruses, such as murine leukemia virus (X-MuLV), bovine viral diarrheal virus (BVDV), and pseudorabies virus (PRV) to demonstrate viral clearance with their various purification methods (Table 3). X-MuLV is model virus commonly used for endogenous retrovirus like particles host cells lines (i.e. CHO or BHK cells) to express the protein drug product. X-MuLValso is also a model for other enveloped viruses including retroviruses, such as the major blood-borne pathogen HIV. BVDV is a model for Flaviviruses, and can represent viruses such as Zika virus (involved in recent outbreaks world-wide) and Hepatitis C virus (HCV). PRV is a model for Hepadnaviruses, and can represent Hepatitis B virus (HBV), which is one of the most common of blood-borne pathogens. In theory, these enveloped viruses are all susceptible to detergent inactivation with N-methylglucamides.

TABLE 3

Enveloped Viruses

| Virus | Family | Genome | Virion size (nm) | Representative of |
|---|---|---|---|---|
| X-MuLV | Retroviridae | ssRNA (+) | 80-130 | Retroviruses (HIV) |
| BVDV | Flaviviridae | ssRNA (+) | 40-50 | Flaviviruses (Zika, Hepatitis C) |
| PRV | Herpesviridae | dsDNA | 150-200 | Hepadnaviruses (Hepatitis B) |

The typical conditions of N-methylglucamide virus inactivation have been assessed using low and high titer stocks of X-MuLV (Table 4). The low-titer stock of X-MuLV was used for the dose-response study and a kinetics study. The high-titer stock of X-MuLV was used for a kinetics study and determination of the high capacity of virus inactivation expressed in log reduction factor (LRF). Other viruses included in Table 4 are the high titer virus stocks of BVDV and PRV, which should also be susceptible to N-methylglucamide detergent inactivation.

TABLE 4

Virus Information

| Virus | Strain | Prepared by | Lot number | Titer ($Log_{10}TCID_{50}$/ml) |
|---|---|---|---|---|
| X-MuLV | pNFS Th-2 | Bayer Pathogen Safety (Berkeley, CA) | Xmv160122.Pure | 6.28 ± 0.27 (low tier) |
| X-MuLV | pNFS Th-1 | BioReliance Inc. (Rockville, MD) | XML101211P | 8.15 ± 0.24 (high tier) |
| X-MuLV | pNFS Th-1 | BioReliance Inc. (Rockville, MD) | XML012908P | 8.17 ± 0.26 (high tier) |
| BVDV | NADL | BioReliance Inc. (Rockville, MD) | BVDV102301P | 8.92 |
| PRV | Aujeszky | BioReliance Inc. (Rockville, MD) | PRV032907P | 8.48 ± 0.26 |

Example 3: Screen of N-Methylglucamide Derivatives

Figure 4:
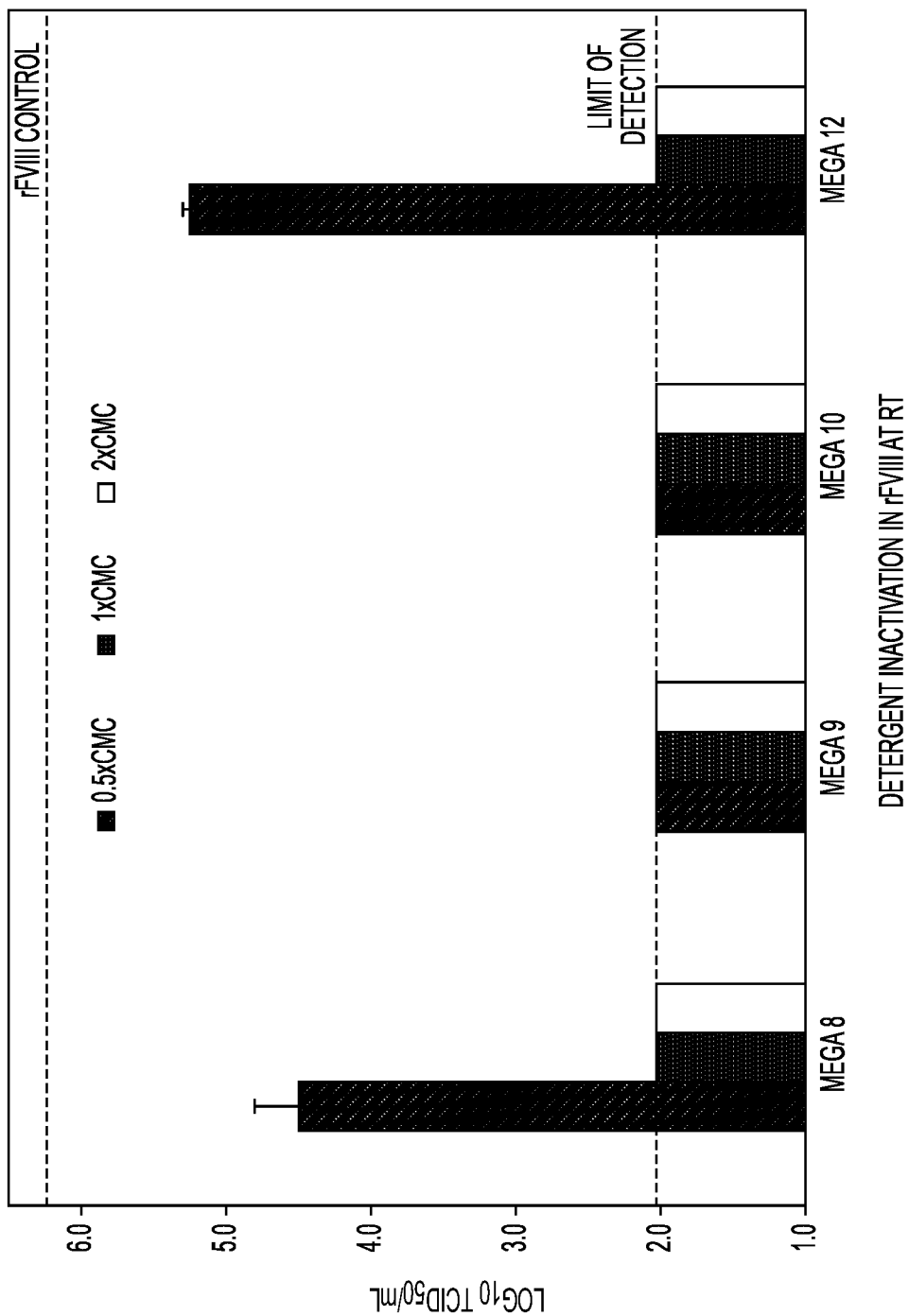
FIG. 4 shows X-MuLV is completely inactivated within 30 minutes at room temperature when recombinant FVIII (rFVIII) is incubated with 0.5×, 1×, 2× of the CMC of Mega 8, and Mega 9. Mega 10, and Mega 12 individually.
Figure 5:
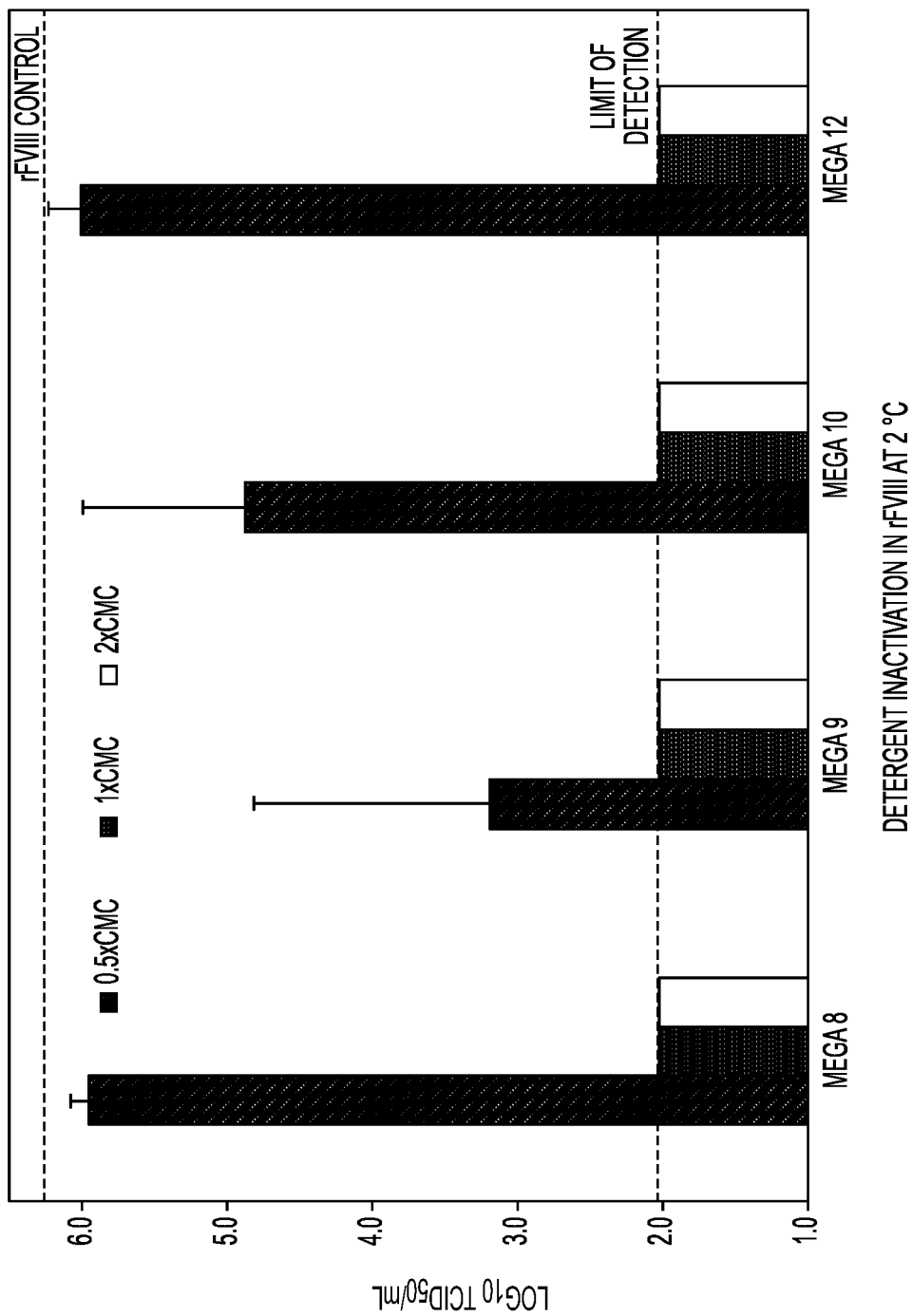
FIG. 5 shows X-MuLV is completely inactivated within 30 minutes at 2.0° C. when recombinant FVIII (rFVIII) is incubated with 1× and 2× of the CMC of each detergent separately (Mega 8, and Mega 9, Mega 10, and Mega 12).
Figure 6:
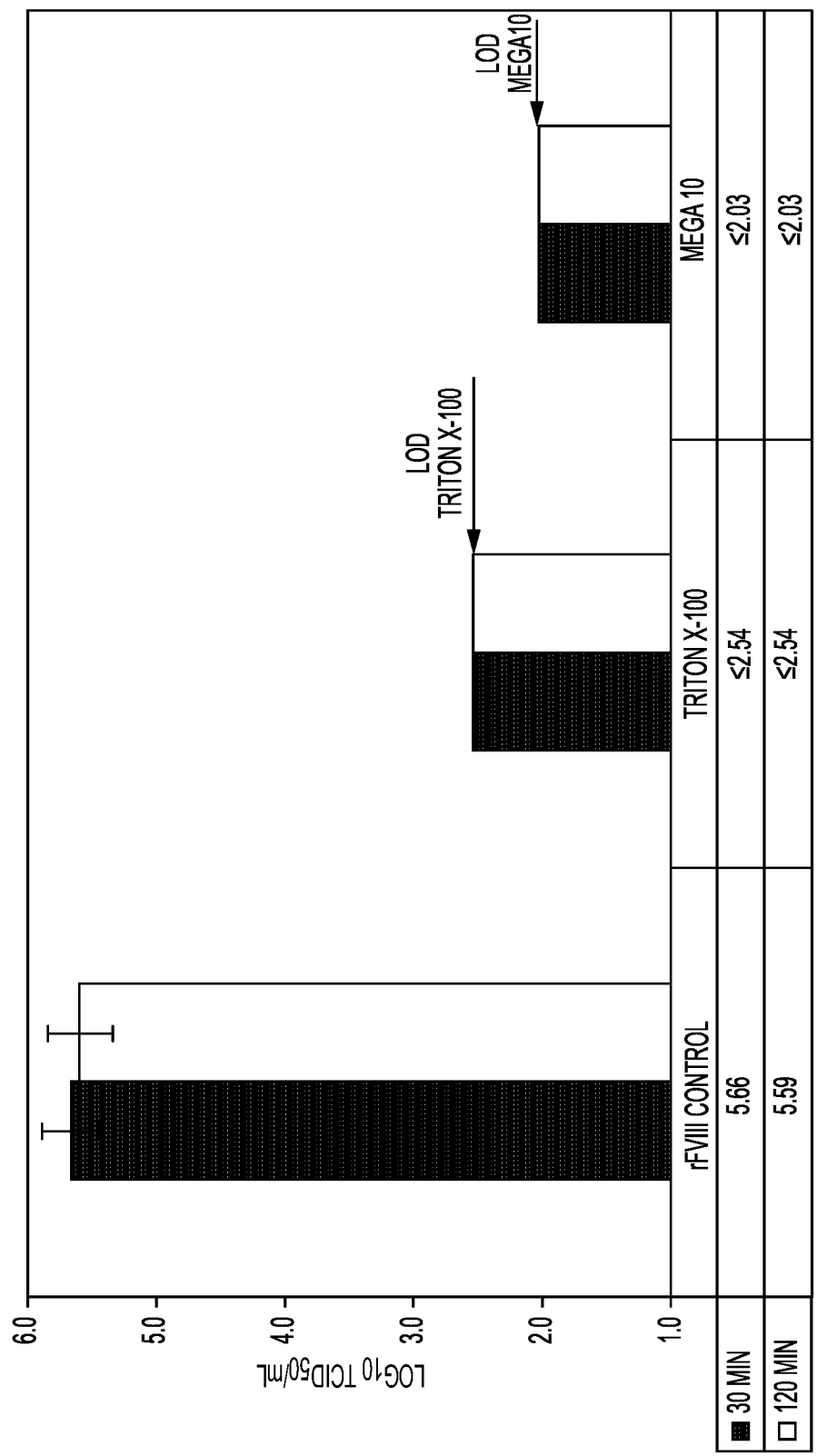
FIG. 6 shows complete X-MuLV inactivation is achieved by 0.3% (w/v) Mega 10 and 0.3% (w/v) Triton X-100 when incubated in recombinant FVIII (rFVIII) at 2.0° C. for 30 minutes demonstrating similar potency of the two detergents.

N-methylglucamide derivatives were tested for their ability to inactivate a high titer stock of X-MuLV. Each detergent (Mega 8, Mega 9, Mega 10, or Mega 12) was tested at 0.5×, 1×, and 2× of the CMC and was mixed with a protein drug (recombinant Factor VIII, rFVIII, antibody or plasma) and spiked with enveloped viruses (i.e. X-MuLV, PRV, or BVDV) and incubated for 30 minutes at RT or 2.0±1.0° C. After the incubation, the reaction was quenched and a $TCID_{50}$ titration assay was performed using the appropriate indicator cells (PG-4, Vero, or EBTr cells). The $TCID_{50}$ answered two questions, which are: Is there any observable virus infection in any of the wells tested? If so, what is the amount of virus (titer) in the tested sample? As expected, after the 30 minutes incubation at 2° C. and room temperature (25° C.), measured titer of the rFVIII controls spiked with X-MuLV was averaged to 6.40 and 6.45 $Log_{10}TCID_{50}$/mL respectively (FIG. 4 and FIG. 5). For each temperature condition, N-methylglucamide (Mega 8, 9, 10 and 12) and its concentration tested inactivated X-MuLV to the limit of detection (LOD) when the N-methylglucamide concentration was 1×CMC or above, indicating complete inactivation of viral infectivity for $\geq 10^{4.3}$-fold or a log reduction factor (LRF) of ≥4.3 (FIG. 4 and FIG. 5. Table 5 and Table 6). It is important to note that the limit of detection (LOD) was ≤2.03 $Log_{10}$ $TCID_{50}$/mL, which is also the titer when no virus is observed. The concentration at 0.5×CMC of Mega 9 and Mega 10 inactivated X-MuLV completely at 25° C. but partially at 2° C. No significant inactivation at 0.5×CMC for Mega 8 and Mega 12 when the treatments were taken place at 25° C. or 2° C. (FIG. 4 and FIG. 5). Inactivation of X-MuLV by N-methylglucamide was as effective as Triton X-100, but less toxicity to the assay indicator cells (FIG. 6). At 0.3% (w/v), both detergents inactivated X-MuLV completely; Mega 10 gave the limit of detection (LOD) of ≤2.03 $TCID_{50}$/mL while Triton X-100 had a LOD of ≤2.54 $TCID_{50}$/mL (FIG. 6). In summary, these results show that these ecofriendly detergents are effective and robust at virus inactivation.

TABLE 5

N-MuLV Inactivation in Recombinant FVIII (rFVIII) at Room Temperature (RT)

| Detergent | Conc. (w/v) | Incubation Time (min) | Infection observed | Log Reduction Factor (LRF)* |
|---|---|---|---|---|
| Mega 8 | 1.81% | 30 | No | ≥4.32 |
| Mega 9 | 0.45% | 30 | No | ≥4.32 |
| Mega 10 | 0.10% | 30 | No | ≥4.32 |
| Mega 12 | 0.014% | 30 | No | ≥4.32 |

*LRF = Titer of the rFVIII (control) - Titer of detergent treatment

TABLE 6

X-MuLV Inactivation in Recombinant FVIII (rFVIII) 2° C.

| Detergent | Conc. (w/v) | Incubation Time (min) | Infection observed | Log Reduction Factor (LRF)* |
|---|---|---|---|---|
| Mega 8 | 1.81% | 30 | No | ≥4.37 |
| Mega 9 | 0.84% | 30 | No | ≥4.37 |
| Mega 10 | 0.20% | 30 | No | ≥4.37 |
| Mega 12 | 0.014% | 30 | No | ≥4.37 |

Example 4: N-Methyglucamides Effect on rFVIII

Figure 7:
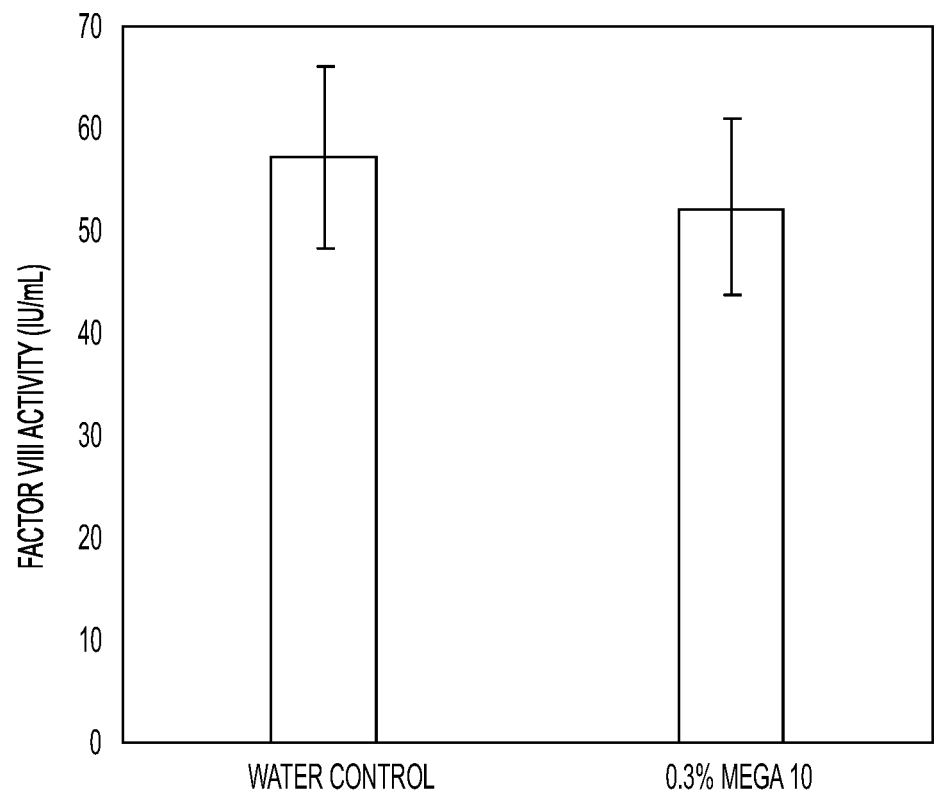
FIG. 7 shows that recombinant FVIII (rFVIII) maintains its activity even after 2 hour incubation with water or Mega 10 at 2.0° C.

After the N-methylglucamide screen, Mega 10 was determined to be the top N-methylglucamide candidate due to high efficacy at lower concentrations (~0.2%) and solubility. To ensure that Mega 10 did not exert negative effects on the protein drug activity, the activity of rFVIII preparation was measured using a chromogenic assay kit. The principle of the assay involves a specific step in the blood clotting mechanism, in which Factor X is converted to Factor Xa leading to the hydrolysis of the chromogenic substrate. This reaction is dependent on the activity of Factor VIII (FVIII) and directly correlates to measurable color intensity. Samples of rFVIII preparation were incubated with 0.3% (weight/volume, w/v) of Mega 10 or 0.3% (volume/volume, v/v) water at 2.0±1.0° C. for 2 hours and the chromogenic assay kit was used to determine the activity of rFVIII. The average activity (IU/mL) of the water control and the Mega 10-treated samples were comparable at 57.19 and 52.26 IU/mL, respectively (FIG. 7). These results indicate that rFVIII activity is maintained even after 2 hours incubation with Mega 10, which is a time point well beyond virus inactivation of 30 minutes. The results demonstrate that Mega 10 is not only effective in inactivating enveloped viruses, but also has no effect on the activity of the protein drug.

Example 5: Dose Response

Figure 8:
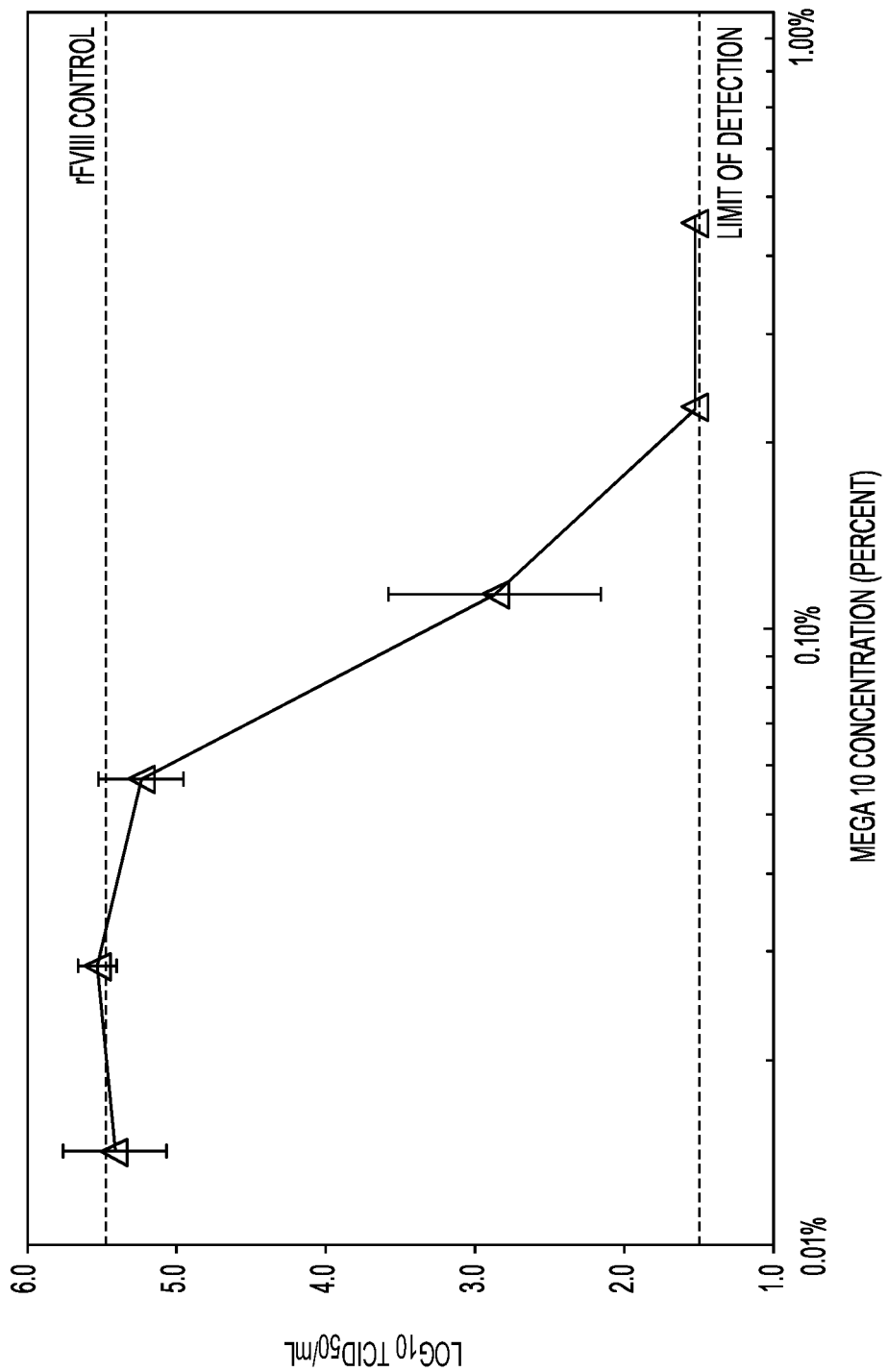
FIG. 8 shows the dose-response of recombinant FVIII (rFVIII) incubated with X-MuLV and increasing concentrations of Mega 10 at 2.0° C. for 30 minutes. The dose response curve shows that as the concentration of the sugar detergent increases, the titer of X-MuLV inversely decreases to the limit of detection (LOD), where no virus was detectable. The rFVIII control (Ctrl) dashed line corresponds to the titer of rFVIII incubated with X-MuLV only.

To determine the lowest effect concentration for Mega 10, a dose response study was performed. Increasing concentrations ranging from 0.014-0.5% (weight/volume, w/v), were incubated with recombinant FVIII (rFVIII) and spiked with X-MuLV (low titer) at 2.0±1.0° C. for 30 minutes. The rFVIII only control was also incubated under the same conditions. After the incubation, all the reactions were quenched and samples were taken for serially dilution in a $TCID_{50}$ assay. For the Mega 10 reactions, the virus titers were comparable to the controls between the concentrations of 0.014-0.06% (w/v), indicating that Mega 10 was not able to inactivate the enveloped viruses at those low concentrations (FIG. 8). As soon as the Mega 10 concentration increased to about 0.11%, the virus titer noticeably decreased to about 2.62 $Log_{10}$ $TCID_{50}$/mL. At approximately 0.23% of Mega 10, the virus titer significantly decreased to levels where no virus infection was observed (FIG. 7 and Table 7). At 0.23% (w/v), the limit of detection (LOD) of Mega 10 was ≤1.52 $Log_{10}$ $TCID_{50}$/mL and, therefore, the LRF was ≥3.96 for mega 10 at 2.0±1.0° C. for 30 minutes (Table 7). In summary, the lowest concentration to quickly and completely inactivate X-MuLV is approximately 0.23% for Mega 10.

TABLE 7

Lowest Effective Concentration of Mega 10

| Detergent or control | Conc. (w/v) | Infection Observed | Log Reduction Factor (LRF)* |
|---|---|---|---|
| Mega 10 | 0.23% | No | ≥3.96 |

*LRF = Titer of the rFVIII (control) - Titer of detergent treatment

Example 6: Kinetics Studies

Figure 9:
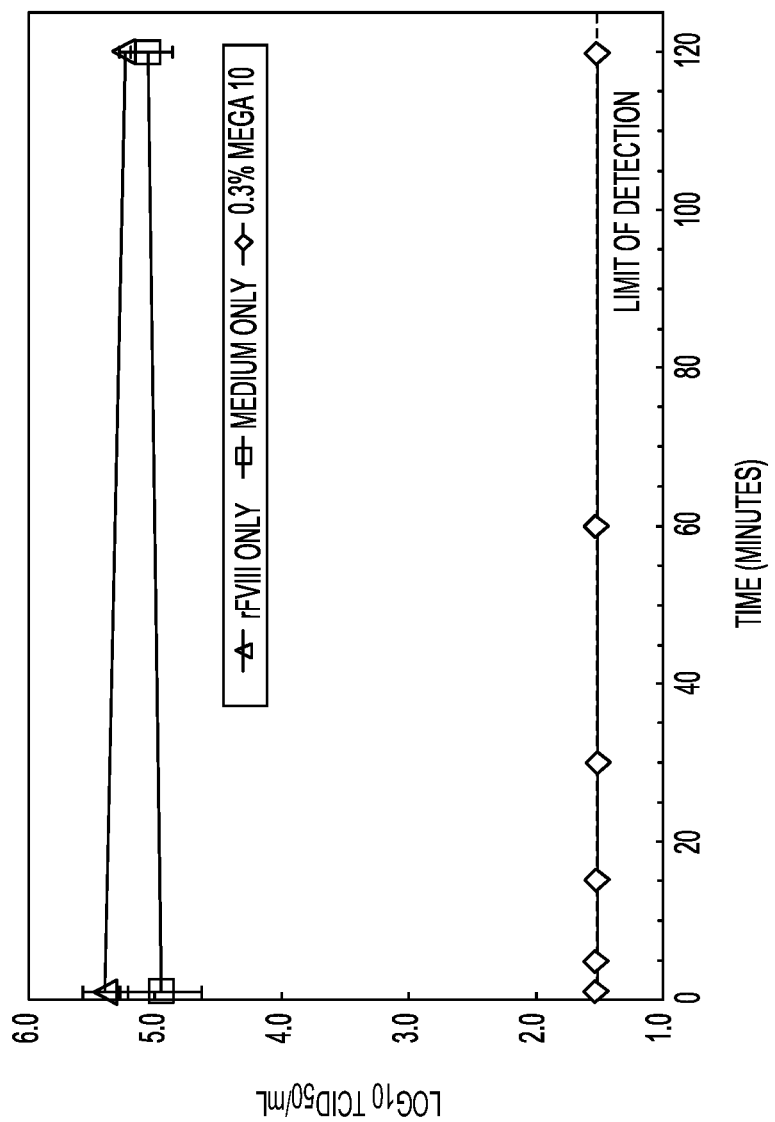
FIG. 9 shows the kinetics of recombinant FVIII (rFVIII) incubated with X-MuLV and 0.3% (w/v) Mega 10 at 2.0° C. for 0, 5, 15, 30, 60, and 120 minutes. The Mega 10 treatments resulted in the immediate decrease (complete inactivation) of virus titer reaching the limit of detection (LOD) where no virus was detectable, which is in contrast to the rFVIII only and medium only controls.

A kinetics study was performed using both low titer and high titer virus preparations to determine how quickly and extensively Mega 10 can inactivate X-MuLV. The kinetics studies entailed multiple concentrations (0.02%, 0.10%, 0.20%, and 0.30% (w/v)), time points (0, 5, 15, 30, 60, and 120 minutes) and a low and high titer X-MuLV stocks. By testing the additional high titer X-MuLV stock, greater assay sensitivity can be achieved, which will be reflected in higher log reduction factor. Mega 10 at 0.3% was incubated with recombinant FVIII (rFVIII) preparation and spiked with low titer X-MuLV virus at 2.0±1.0° C. for 0, 5, 15, 30, 60, and 120 minutes. Then, the reaction samples were quenched and samples were taken for the TCIDso assay. The results for Mega 10 show that virus was immediately inactivated after mixing X-MuLV with detergent containing sample (t~0) (FIG. 9). No virus infectivity was detected at any time point assayed, again indicating complete inactivation with the limit of detection reaching ≤1.52 $Log_{10}$ $TCID_{50}$/mL and a log reduction factor of ≥3.80.

TABLE 8

N-Methylglucamides Inactivated Low Titer X-MuLV Immediately

| Detergent or Control | Conc. (w/v) | Incubation Time (min) | Infection observed | Log Reduction Factor (LRF)* |
|---|---|---|---|---|
| Mega 10 | 0.3% | 0 | No | ≥3.80 |

*LRF = Titer of the rFVIII (control) - Titer of detergent treatment

Figure 10:
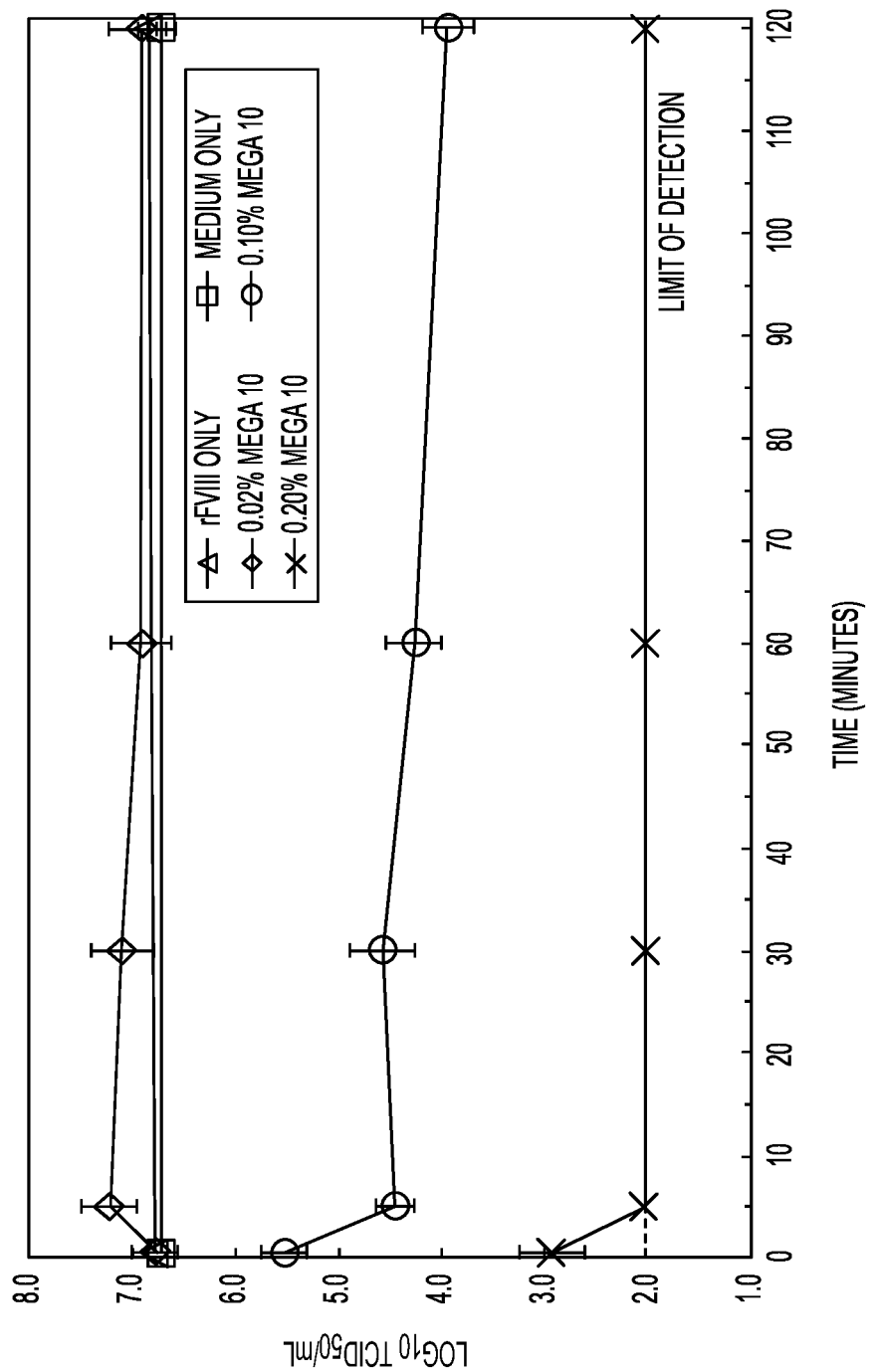
FIG. 10 shows the kinetics of recombinant FVIII (rFVIII) incubated with a high-titer stock of X-MuLV with 0.02%, 0.10% or 0.20% (w/v) Mega 10 at 2.0° C. for 0, 5, 30, 60, and 120 minutes. Mega 10 at 0.10% (w/v) resulted in a decrease of virus titer whereas 0.20% (w/v) resulted in the immediate decrease (complete inactivation) of virus titer reaching limit of detection (LOD) within 5 minutes where no virus was detectable, in contrast to the 0.02% (w/v) of Mega 10, rFVIII and medium only control samples where no virus inactivation was observed.

Upon repeating a similar experiment with high titer X-MuLV stock and multiple Mega 10 concentrations, partial inactivation of virus was observed at 0 minutes (t~0) (0.20% Mega 10) with complete inactivation achieved by 5 minutes (0.20% Mega 10) (FIG. 10). Notably, at 0.20% of Mega 10, no live virus was observed from 5 to 120 minutes of incubation with a limit of detection of 52.03 $Log_{10}$ $TCID_{50}$/mL, leading to a viral infectivity reduction of ≥$10^{4.80}$-fold (Table 9). This example has demonstrated that Mega 10 is highly effective at low concentrations within a quick action that ranges from 0-5 minutes.

TABLE 9

N-Methylglumacide Inactivated High Titer X-MuLV Quickly

| Detergent or Control | Conc. (w/v) | Incubation Time (min) | Infection observed | Log Reduction Factor (LRF)* |
|---|---|---|---|---|
| Mega 10 | 0.2% | 5 | No | ≥4.80 |

*LRF = Titer of the rFVIII (control) - Titer of detergent treatment

Example 7: Mega 10 Lot-To-Lot Comparison

Figure 11:
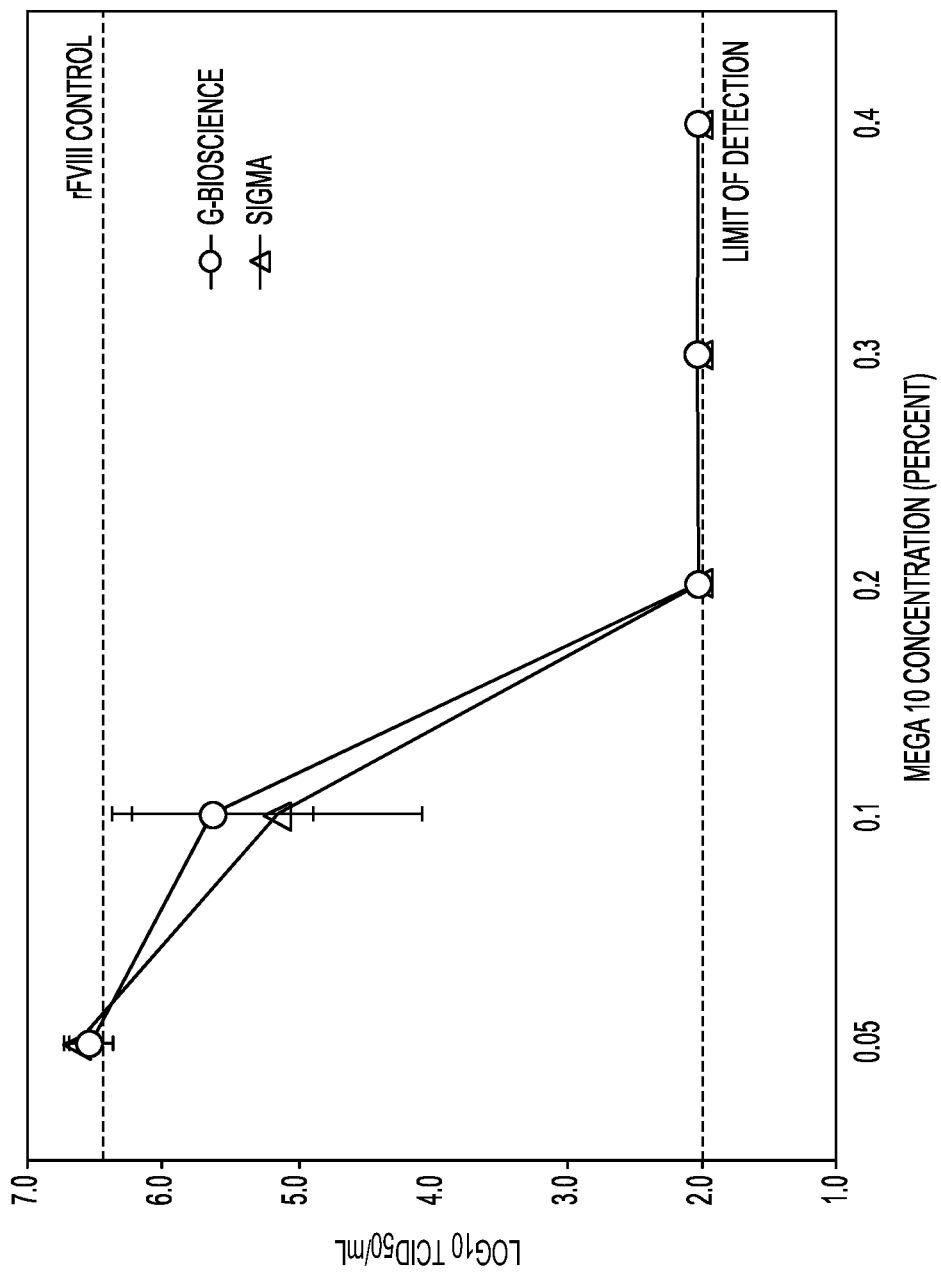
FIG. 11 shows that different manufactured Mega 10 molecules yield similar and reproducible dose response results.

To ensure consistency of Mega 10 across multiple vendors and manufacturing lots, a dose response comparing detergent products from G-Bioscience and Sigma was performed. For each vendor, samples were prepared at multiple concentrations (0.05, 0.1, 0.2, 0.3, 0.4% w/v) and were incubated with recombinant FVIII (rFVIII) and spiked with X-MuLV (high titer) at 2.0±1.0° C. for 30 minutes. An rFVIII only control was also incubated under the same conditions. After incubation, all reactions were quenched and tittered for a TCIDso assay. For each G-Bioscience and Sigma produced Mega 10 sample, viral titers were consistent with each other at their respective concentration levels (FIG. 11). The X-MuLV inactivation profile shows the Mega 10 products from both sources are comparable. The samples treated with 0.2-0.4% Mega 10 of each product gave a complete inactivation of ≤2.03 $Log_{10}$ $TCID_{50}$/mL and a LRF of ≥24.45. In summary, Mega 10 sourced from different sources yielded results consistent with each other and with previous data.

Example 8: Inactivation of More Enveloped Viruses (BVDV and PRV) in Recombinant FVIII by N-Methylglucamides To further determine whether potent and fast X-MuLV inactivation by N-methylglcamides works equally with other enveloped viruses, Mega 9 and 10 were assessed for their ability to inactivate BVDV and PRV in recombinant FVIII (rFVIII) solutions.

BVDV inactivation by Mega 9 and 10 was determined via a dose response study. Samples of rFVIII containing Mega 9 at 0.5, 0.8, and 1.0% (w/v) and Mega 10 at 0.2, 0.3, and 0.4% (w/v) were spiked with BVDV stock at 1:11 and incubated at 2.0±1.0° C. for 30 minutes. After incubation, samples were quenched and titrated to perform a $TCID_{50}$ assaying using EBTr indicator cells. Results showed that Mega 9 was able to inactivate BVDV to the detection limit (≤2.03 $Log_{10}$ $TCID_{50}$/mL) only with concentration of 1.0%. Mega 10 was able to completely inactivate BVDV at 0.2, 0.3, and 0.4% (w/v). Both detergents were capable of reducing BDVD infectivity by ≥$10^{5.14}$-fold.

Figure 12:
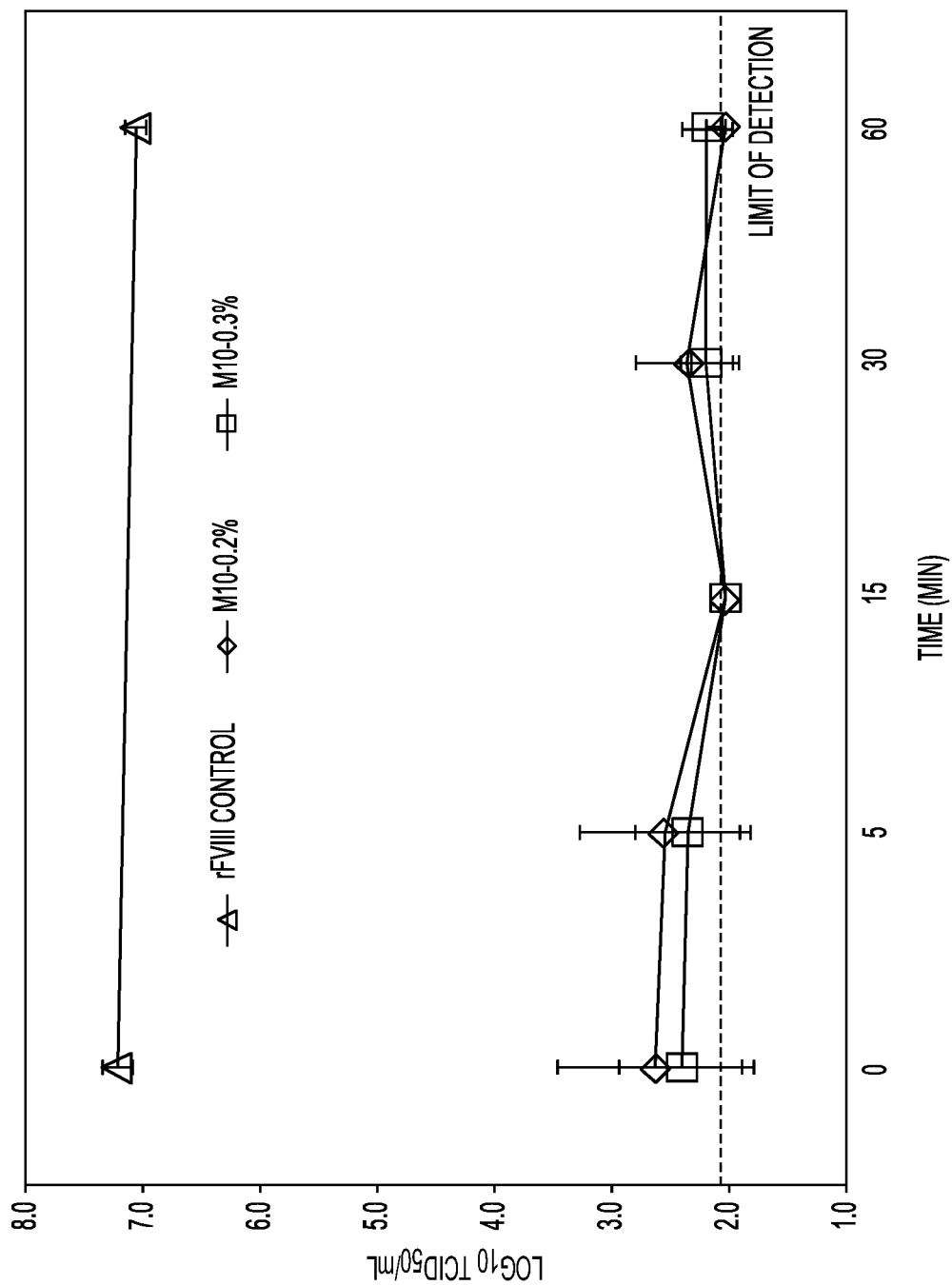
FIG. 12 shows porcine pseudorabies virus (PRV) is inactivated to the limit of detection by 0.2 and 0.3 (w/v) Mega 10 at 2.0° C. within 15 minutes when incubated in recombinant FVIII (rFVIII).

PRV was spiked (1:11) into rFVIII preparations containing Mega 10 at 0.2 or 0.3% (w/v) and assayed with time points at 0, 5, 15, 30, and 60 minutes at 2.0±1.0° C. After incubation, samples were quenched and titrated in a $TCID_{50}$ assay using Vero indicator cells. Results showed that both 0.2 and 0.3% Mega 10 are capable of reducing viral infectivity≥immediately by $10^{4.5}$-fold or higher and reached the limit of detection (≤2.03 $Log_{10}$ $TCID_{50}$/mL) at 15 minutes, with a reduction of infectivity ≥$10^{5.10}$-fold for both concentrations of Mega 10 (FIG. 12).

Figure 13:
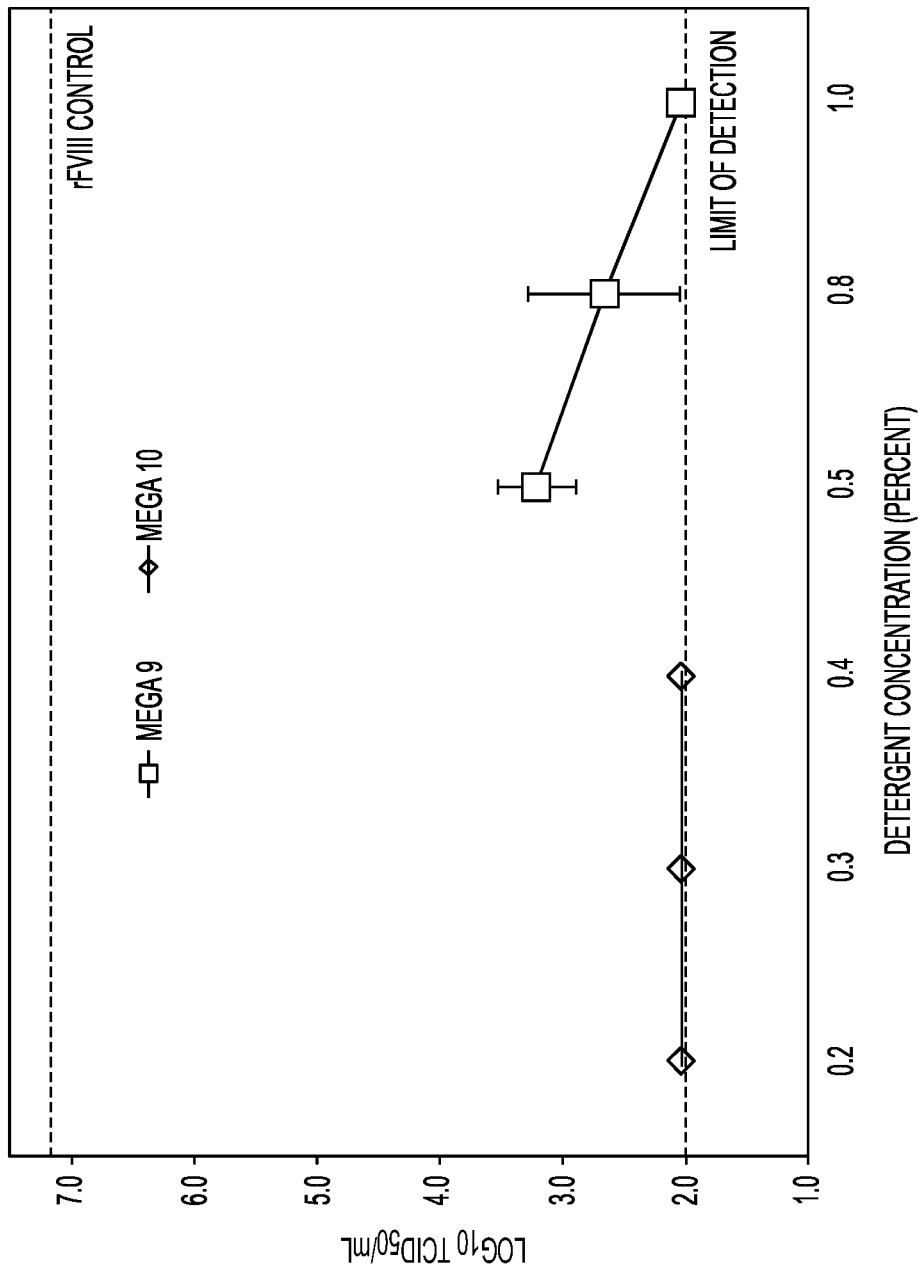
FIG. 13 shows bovine viral diarrhea virus (BVDV) is completely inactivated to the limit of detection by 0.2, 0.3, and 0.4 (w/v) Mega 10 and by 1.0% (w/v) Mega 9 when incubated in recombinant FVIII (rFVIII) for at 2.0° C. 30 minutes.

In summary, Mega 10 is capable of inactivating PRV at 0.2% within 15 minutes and BVDV at 0.2% immediately after mixing, representing a ≥$10^{5.14}$-fold reduction of BVDV infectivity. Mega 9 was effective in inactivating BVDV to the LOD at 1.0% (w/v) within 30 minutes of treatment. Both Mega 10 and Mega 9 were capable of inactivating BVDV to the LOD, representing a ≥$10^{5.14}$-fold reduction of BVDV infectivity. Mega 10 inactivation of BVDV is much faster and lower concentration than Mega 9. These results demonstrated that the N-methylglucamides are able to inactivate enveloped viruses effectively regardless of the families and species of the viruses (FIG. 13).

Figure 15:
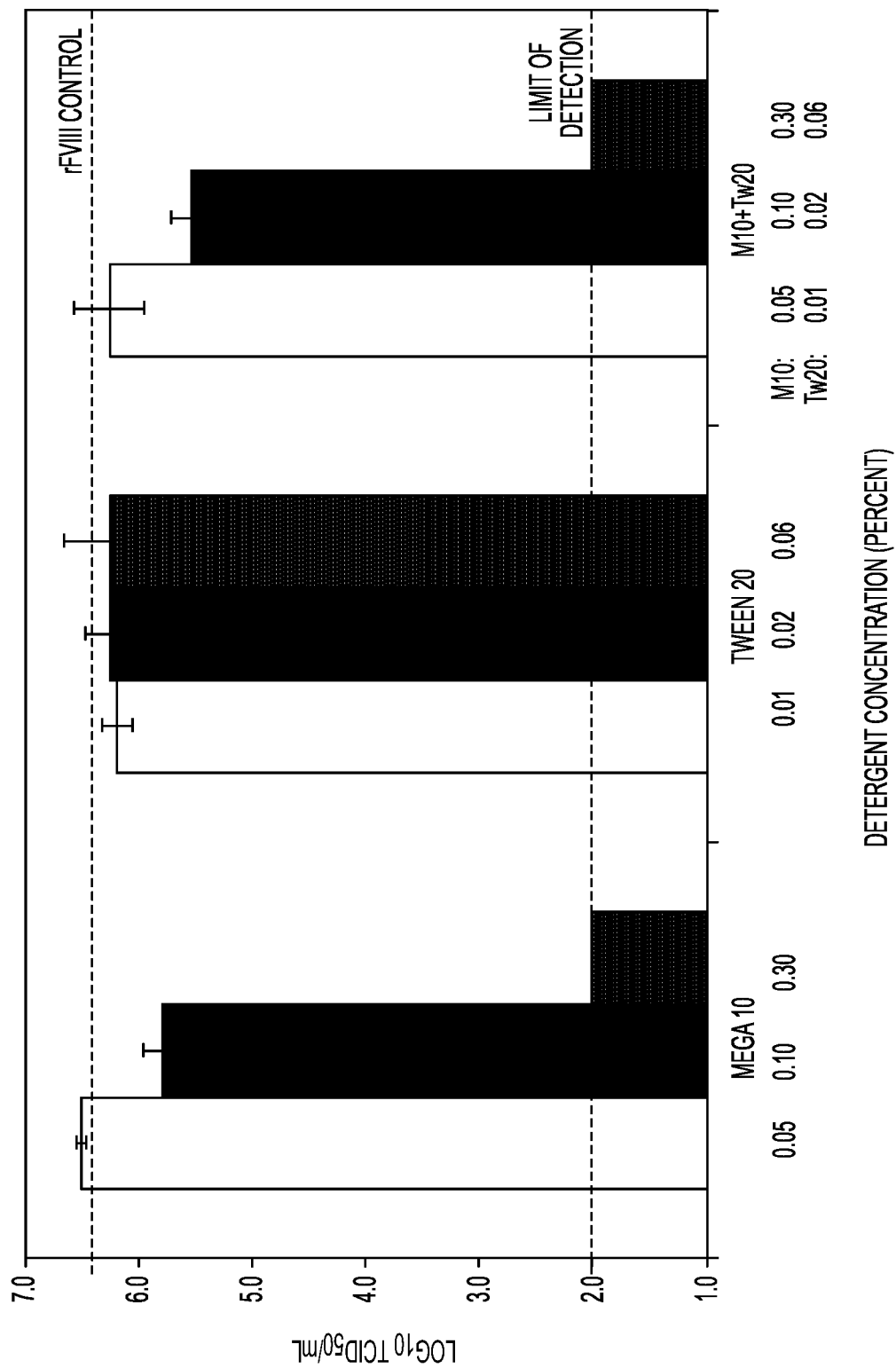
FIG. 15 shows X-MuLV inactivation with Mega 10 (M10) alone, Tween 20 (Tw20) alone, and a Mega 10 with Tw20 mixture at concentrations of 0.05% (w/v), 0.10% (w/v), or 0.30% (w/v) Mega 10 with or without 0.01% (w/v), 0.02% (w/v), or 0.06% (w/v) Tw20. At concentrations of 0.30% (w/v) M10 alone or a 0.30% (w/v) M10+0.06% (w/v) Tw20 mixture, X-MuLV was completely inactivated within 30 min.
Figure 16:
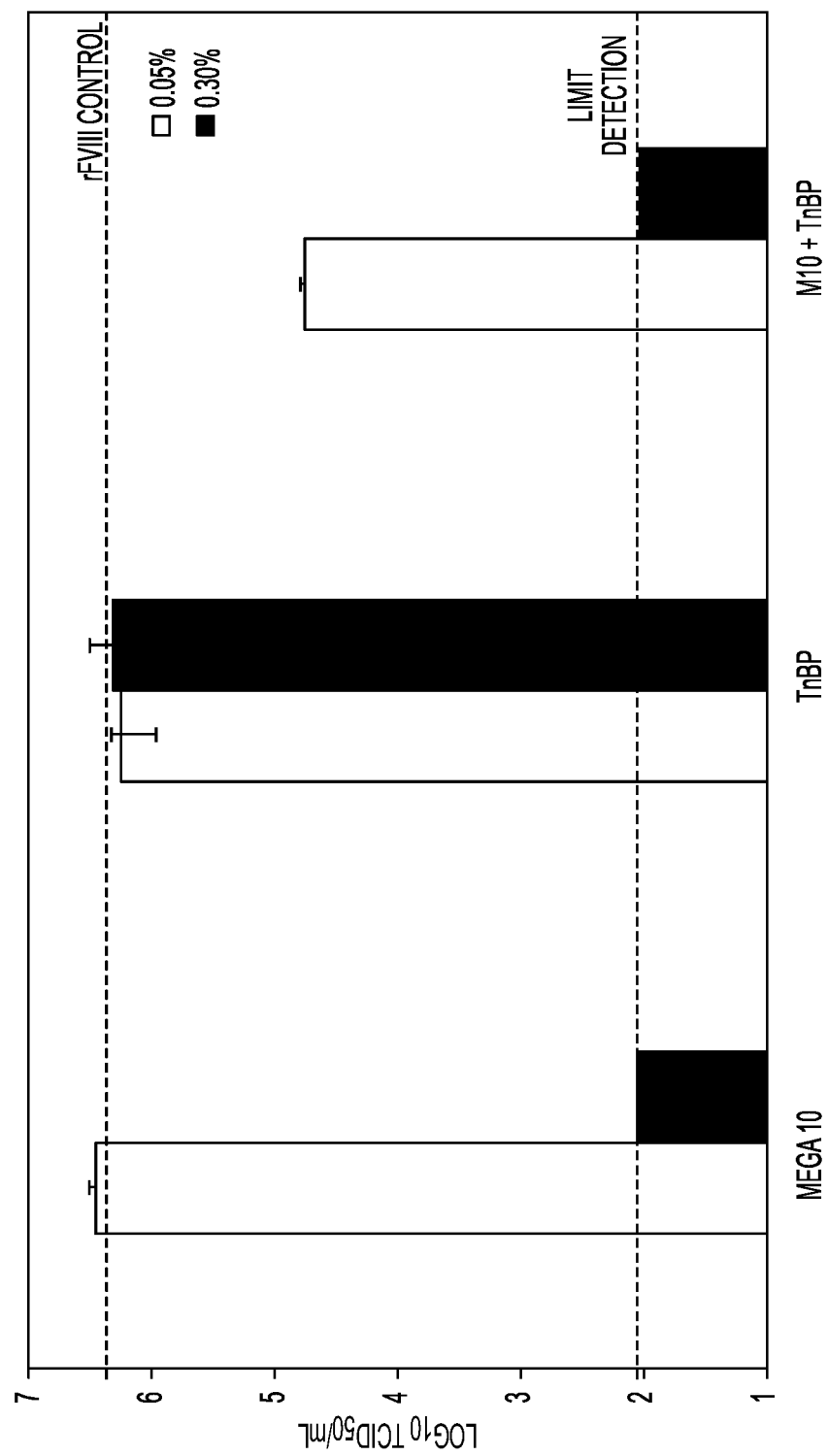
FIG. 16 shows X-MuLV inactivation with Mega 10 (M10) alone, tri(n-butyl)phosphate (TnBP) alone, and a Mega 10 with TnBP mixture (1:1) at concentrations of 0.05% (w/v) or 0.30% (w/v). At concentrations of 0.30% (w/v) M10 alone or a 0.30% (w/v) M10+0.30% (w/v) TnBP mixture, X-MuLV was completely inactivated within 30 min. Interestingly, there was a reduction in virus titer for 0.05% (w/v) M 10+0.05% (w/v) TnBP (but not complete inactivation), indicating that there could be a synergistic effect between Mega 10 and TnBP. The rest of the detergent treatments yielded no virus inactivation as the viral titers were comparable to the rFVIII control (with no detergent).
Figure 17:
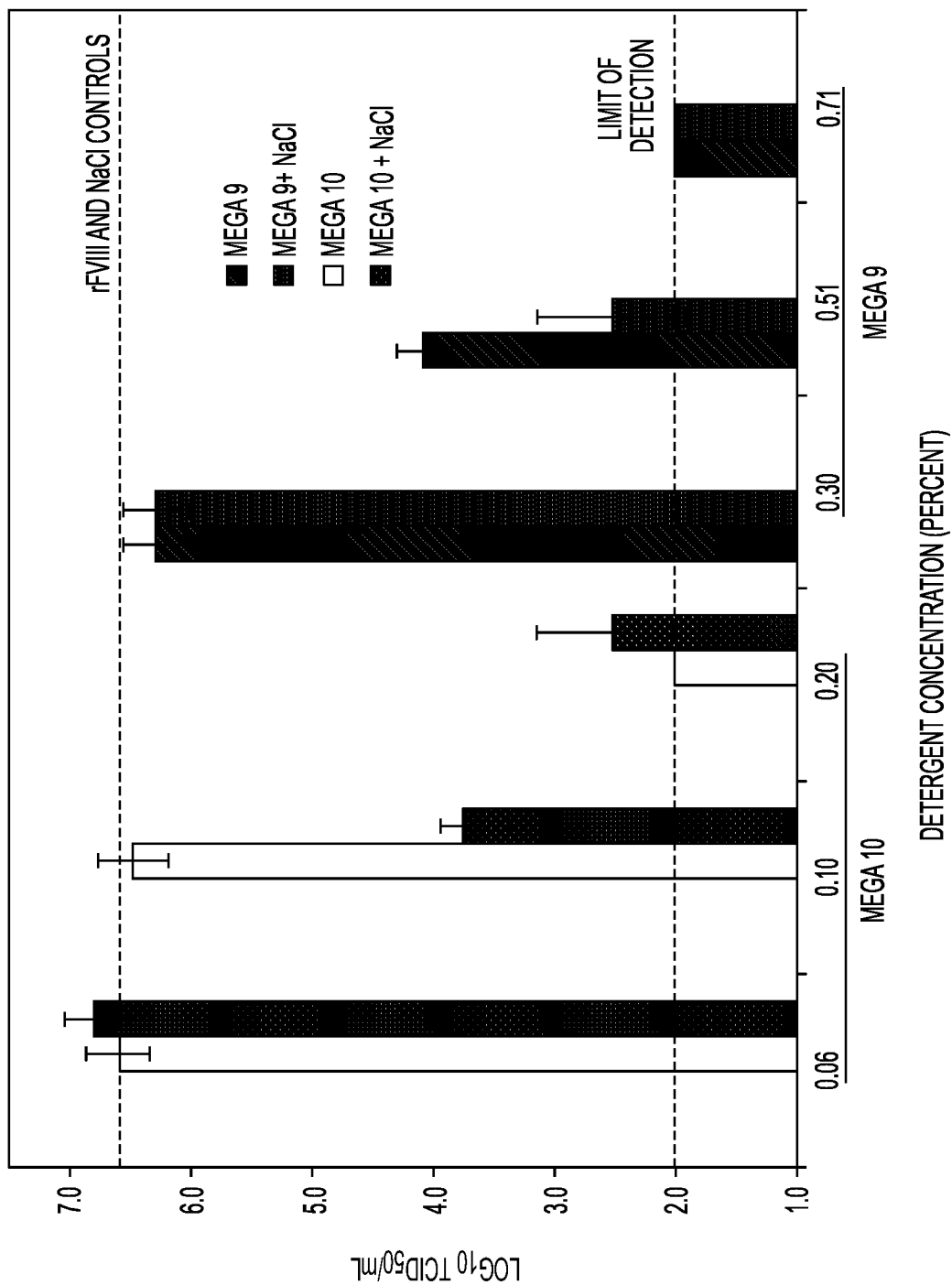
FIG. 17 shows X-MuLV inactivation with 0.06% (w/v), 0.10% (w/v), or 0.20% (w/v) Mega 10 or 0.30% (w/v), 0.51% (w/v), or 0.71% (w/v) Mega 9 with or without 550 mM NaCl. At concentrations of 0.20% (w/v) Mega 10 alone, 0.20% (w/v) Mega 10+NaCl. and 0.71% (w/v) Mega 9 with and without 500 mM NaCl, X-MuLV was significantly inactivated. There was a reduction in virus titer for 0.10% (w/v) Mega 10+550 mM NaCl and 0.51% (w/v) Mega 9+500 mM NaCl, indicating that there could be some synergistic effect between Mega 10 or Mega 9 and NaCl. The rest of the detergent treatments yielded no virus inactivation as the viral titers were comparable to the rFVIII control (with no detergent) and NaCl control (with no detergent).

Methylglucamides were tested with other compounds to determine potential synergistic effects on viral inactivation. Methylglucamides were mixed with and without Tween 20 (Tw20) detergent, tri(n-butyl)phosphate (TnBP) solvent, or sodium chloride (NaCl) salt and incubated with X-MuLV. Then, the titers of each samples or controls were assayed using a $TCID_{50}$ assay previously described. For each experiment (FIGS. 15, 16 and 17), the controls consisted of rFVIII spiked with X-MuLV with no detergent, and the yielded titers within the expected range of about 6.5 $log_{10}$ $TCID_{50}$/ml. Concentrations of 0.05% (w/v), 0.10% (w/v), or 0.30% (w/v) Mega 10 were mixed with the commonly used Tw20 detergent at 0.01% (w/v), 0.02% (w/v), or 0.06% (w/v), virus titers were comparable to the Mega 10 alone (FIG. 15). Therefore, Mega 10+Tw20 did not further enhance viral inactivation. Concentrations of 0.05% (w/v) or 0.30% (w/v) Mega 10 was mixed with the commonly used TnBP solvent at 0.05% (w/v) or 0.30% (w/v) (respectively), virus titers decreased slightly with 0.05% (w/v) Mega 10+0.05% (w/v) TnBP compared to 0.05% Mega 10 alone (FIG. 16). Therefore, Mega 10+TnBP slightly enhanced viral inactivation. Lastly, concentrations of 0.10% (w/v) Mega 10 or 0.51% (w/v) Mega 9 was mixed with 500 mM NaCl, virus titers decreased compared to than 0.10% (w/v) Mega 10 or 0.51% (w/v) Mega 9 alone (FIG. 17). Therefore, Mega 10 or Mega 9+NaCl enhanced viral inactivation. Taken together, the results show that synergistic effects are observed between methylglucamides and TnBP or NaCl and can be used to enhance the viral inactivation efficiency of methylglucamides.

Figure 14:
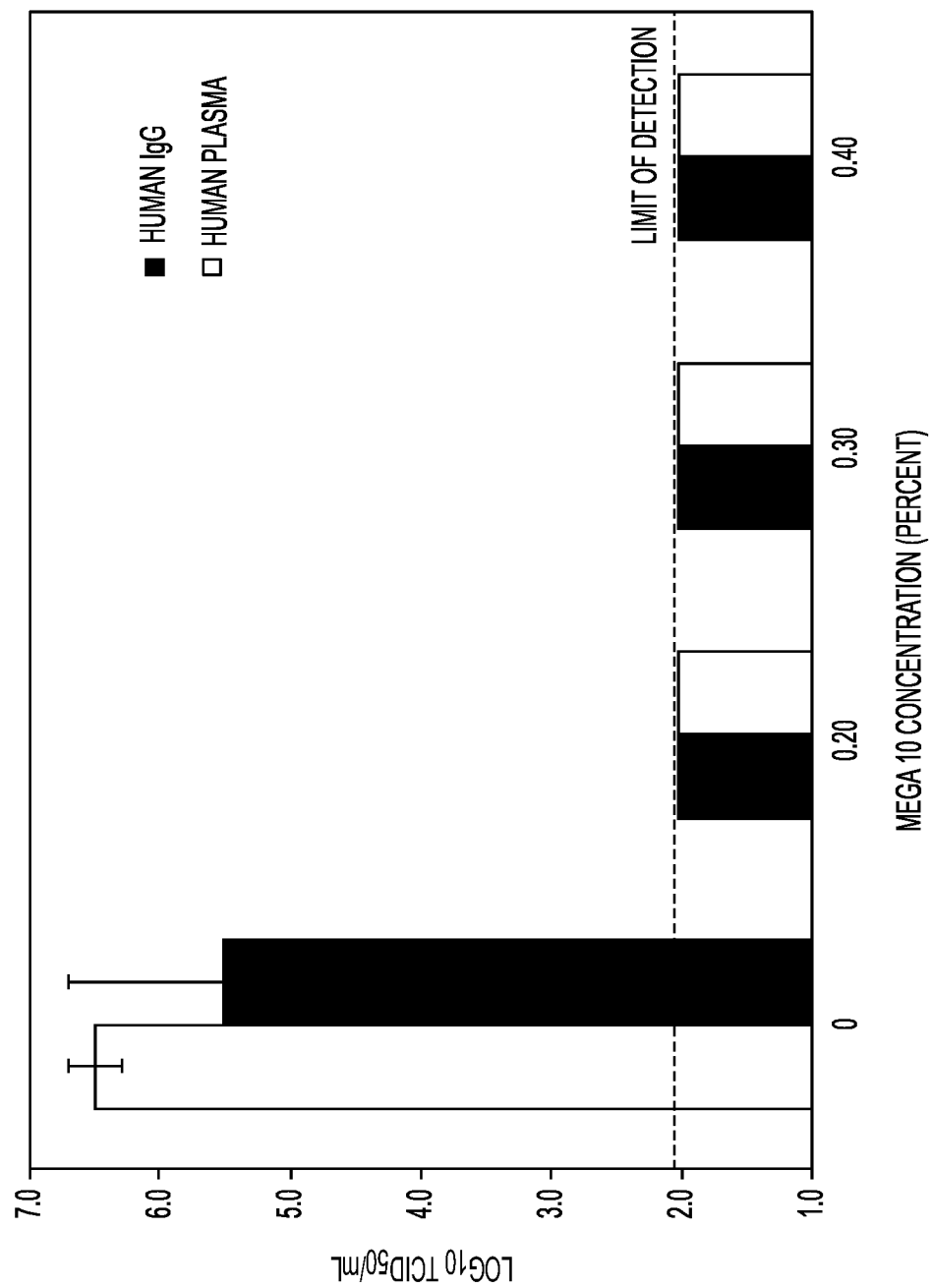
FIG. 14 shows X-MuLV is completely inactivated to the limit of detection when incubated with 0.2, 0.3, and 0.4% (w/v) Mega 10 in human immunoglobulin G (IgG) and human plasma protein solutions at 2.0° C. for 30 minutes. Both protein solutions were prepared so that each had a final concentration of 30 mg/mL.

Example 9: Inactivation of Enveloped Viruses (X-MuLV) in Human Antibody Solutions and Human Plasma by N-Methylglucamides To this point, Mega 10 has been shown to be a potent inactivator of multiple enveloped viruses in recombinant FVIII protein matrix. To assess if Mega 10 is effective in other plasma related protein matrices. X-MuLV inactivation was carried out in human immunoglobulin G (IgG) and plasma solutions. Each protein matrix sample was prepared at 30 mg/mL containing 0.2, 0.3, and 0.4% (w/v) of Mega 10 and spiked with X-MuLV stock (1:11) and incubated at 2.0±1.0° C. for 30 minutes. After incubation, samples were quenched and serially diluted in a $TCID_{50}$ assay using PG-4 indicator cells. Results showed that in both the human IgG and human plasma samples, Mega 10 was capable of inactivating X-MuLV to the limit of detection (≤2.03 $Log_{10}$ $TCID_{50}$/mL) with a reduction of X-MuLV infectivity to ≥$10^{4.46}$-foldin IgG and ≥$10^{3.50}$-fold in human plasma solutions (FIG. 14). The difference in values of virus infectivity reduction for the two protein matrices was due to the fact that the human plasma sample had a lower positive control viral titer compared to that of the IgG positive control. The believed cause of this discrepancy stemmed from the plasma not being heat inactivated prior to performing the experiment, resulting in complement mediated viral inactivation nonspecifically. In summary, Mega 10 is capable of inactivating X-MuLV as effectively and quickly in multiple blood related protein matrices as in rFVIII protein solutions, indicating virus inactivation by N-methylglucamides are not affected by the biological product types, sources and concentrations.

This method of inactivating viruses with N-methylglucamides is applicable to the purification process of biologically-active drugs such as protein subunits, proteins (enzymes, factors, etc.), recombinant proteins, or antibodies or human blood/plasma derived therapeutics. The environmentally safe detergents used in this method are sugar based multiple N-methylglucamide homologs, consisting of a hydrophilic glucose moiety and hydrophobic fatty acid tail, linked by an amide bond. Since there are no known toxic intermediates such as octylphenol in N-methylglucamides, it eliminates the risks associated with environmental concerns. Additionally, these sugar-based detergents are nonionic by nature, which has been demonstrated to show no disruption to the drug protein of interest. By nature, N-methylglucamides should have no effect on non-enveloped viruses and nucleic acid preparations. This method involves the incubation of the N-methylglucamide with protein drug product to inactivate any potential enveloped virus contaminant. To assess viral reduction by this method, multiple model enveloped viruses (e.g. xenotropic leukemia virus, pseudorabies virus and bovine viral diarrheal virus) were spiked into protein drug samples (e.g. native proteins, recombinant proteins, antibodies, human plasma) separately and incubated with N-methylglucamides. After the incubation, a $TCID_{50}$ assay was performed to determine the viral infectivity titer. Furthermore, inactivation of enveloped viruses with N-methylglucamides is comparable to that of the well documented virus inactivation detergent Triton X-100. Taken together, these excellent characteristics make N-methylglucamides a powerful tool in the purification process of biologically-derived drug products.

We claim:

1. A method of purifying a biological product solution having an unidentified enveloped virus contaminant comprising;
    (a) incubating the biological product solution at 2.0±1.0° C. for 30 minutes with an N-methylglucamide solution in a 0.1 to 0.3% (w/v) concentration until an enveloped virus contaminant present in the biological product solution is inactivated to form an inactivated virus contaminant; and
    (b) purifying the biological product solution of step (a) to remove the inactivated virus contaminant.

2. A method as recited in claim 1, wherein the enveloped virus comprises a single stranded RNA virus genome.

3. A method as recited in claim 1, wherein the enveloped virus comprises a double stranded RNA virus genome.

4. A method as recited in claim 1, therein the enveloped virus comprises a double stranded DNA virus genome.

5. A method as recited in claim 3, wherein the double stranded RNA virus is a retrovirus.

6. A method as recited in claim 1, wherein the virus belongs within one or more of the following viral families selected from the group consisting of: Retroviridae, Flaviviridae, Togaviridae, Coronaviridae, Filoviridae, Rhabdoviridae, Bunyaviriae, Orthomyxoviridae, Paramyxoviridea, Arenaviridae, Hepadnaviridae, Herpesviridae, Baculoviridae and Poxviridae.

7. A method as recited in claim 1, wherein the enveloped virus comprises a xenotropic leukemia virus, pseudorabies virus, or bovine viral diarrhea virus.

8. A method as recited in claim 1, wherein the N-methylglucamide is comprises a fatty acid hydrophobic chain with n carbons, where n≥3 and linked by an amide bond to an acyclic, hydrophilic glucose sugar moiety.

9. A method as recited in claim 1, wherein the N-methylglucamide is selected from the group consisting of Mega 8, Mega 9, Mega 10, Mega 11, and Mega 12.

10. A method as recited in claim 1, wherein the biological product is selected from the group consisting of recombinant proteins, antibodies, cytokines, plasma proteins, vaccine solution, nucleic acid therapeutics and gene therapy products.

11. A method as recited in claim 1, wherein the biological product was produced from a eukaryotic cell.

12. A method as recited in claim 11, wherein the eukaryotic cell is a mammalian cell.

13. A method as recited in claim 1, wherein the biological product was produced from a prokaryotic cell.

* * * * *